United States Patent
Nair et al.

(10) Patent No.: US 10,213,507 B2
(45) Date of Patent: Feb. 26, 2019

(54) COMPOSITIONS AND METHODS FOR TREATING HIV-ASSOCIATED NEUROCOGNITIVE DISORDERS

(71) Applicants: Madhavan Nair, Coral Gables, FL (US); Sneham Tiwari, Miami, FL (US); Adriana Yndart Arias, Miami, FL (US)

(72) Inventors: Madhavan Nair, Coral Gables, FL (US); Sneham Tiwari, Miami, FL (US); Adriana Yndart Arias, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/456,039

(22) Filed: Mar. 10, 2017

(65) Prior Publication Data
US 2018/0256720 A1    Sep. 13, 2018

(51) Int. Cl.
| | |
|---|---|
| *A61K 9/127* | (2006.01) |
| *A61K 41/00* | (2006.01) |
| *A61K 9/00* | (2006.01) |
| *A61K 47/48* | (2006.01) |
| *A61K 31/495* | (2006.01) |
| *A61K 31/585* | (2006.01) |
| *C12N 15/113* | (2010.01) |
| *A61K 47/69* | (2017.01) |

(52) U.S. Cl.
CPC ............ *A61K 41/00* (2013.01); *A61K 9/0085* (2013.01); *A61K 9/1271* (2013.01); *A61K 31/495* (2013.01); *A61K 31/585* (2013.01); *A61K 47/48015* (2013.01); *A61K 47/48884* (2013.01); *C12N 15/1137* (2013.01); *A61K 47/6929* (2017.08); *C12N 2310/141* (2013.01); *C12N 2310/351* (2013.01); *C12N 2320/31* (2013.01); *C12N 2320/32* (2013.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

| | | | | |
|---|---|---|---|---|
| 2003/0171347 | A1* | 9/2003 | Matsumoto ........... | C07C 211/10 514/183 |
| 2007/0208009 | A1* | 9/2007 | Hoetelmans ......... | A61K 31/343 514/220 |
| 2015/0283368 | A1* | 10/2015 | Khizroev ........... | A61K 31/7072 600/12 |

OTHER PUBLICATIONS

KW Menting, JAHR Claassen. "B-secretase inhibitor; a promising novel therapeutic drug in Alzheimer's disease." Frontiers in Aging Neuroscience, vol. 6 Article 165, Jul. 2014, pp. 1-9.*
Y Nishikawa, D Okuzaki, K Fukushima, S Mukai, S Ohno, Y Ozaki, N Yabuta, H Nojima. "Withaferin A Induces Cell Death Selectively in Androgen-Independent Prostate Cancer Cells but Not in Normal Fibroblast Cells." PLOS ONE, DOI:10.1371/journal.pone.0134137, Jul. 31, 2015, pp. 1/20 to 20/20.*
M Nair, RD Jayant, A Kaushik, V Sagar. "Getting into the brain: Potential of nanotechnology in the management of NeuroAIDS." Advanced Drug Delivery Reviews, vol. 103, 2016, pp. 202-217. Available online Mar. 2, 2016.*
R Vassar. "BACE1 inhibitor drugs in clinical trials for Alzheimer's disease." Alzheimer's Research & Therapy, vol. 6:89, 2014, pp. 1-14.*
MM Esiri, SC Biddolph, CS Morris. "Prevalence of Alzheimer plaques in AIDS." Journal of Neurology, Neurosurgery and Psychiatry, vol. 65, 1998, pp. 29-33.*
M Fiala, XH Gan, L Zhang, SD House, T Newton, MC Graves, P Shapshak, M Sins, KS Kim, M Witte, SL Chang. "Cocaine Enhances Monocyte Migration Across the Blood-Brain Barrier." Drugs of Abuse, Immunomodulation, and Aids, edited by Friedman etal. Plenum Press, New York, 1998, pp. 199-205.*
WX Wang, BW Rajeev, AJ Stromberg, N Ren, G Tang, Q Huang, I Rigoutsos, PT Nelson. "The Expression of MicroRNA miR-107 Decreases Early in Alzheimer's Disease and May Accelerate Disease Progression through Regulation of B-Site Amyloid Precursor Protein-Cleaving Enzyme 1." The Journal of Neuroscience, vol. 28(5), 2008, pp. 1213-1223.*
JV Georgieva, D Hoekstra, IS Zuhorn. "Smuggling Drugs into the Brain: An Overview of Ligands Targeting Transcytosis for Drug Delivery across the Blood—Brain Barrier." Pharmaceutics, vol. 6, 2014, pp. 557-583.*
KRV Kurapati, T Samikkannu, VSR Atluri, E Kaftanovskaya, A Yndart, MPN Nair. "B-Amyloid1-42, HIV-1 Ba-L (Clade B) Infection and Drugs of Abuse Induced Degeneration in Human Neuronal Cells and Protective Effects of Ashwagandha (Withania somnifera) and Its Constituent Withanolide A." Plos One, DOI:10.1371, Nov. 21, 2014, pp. 1-23.*

(Continued)

*Primary Examiner* — Isaac Shomer
(74) *Attorney, Agent, or Firm* — Saliwanchik, Lloyd & Eisenschenk

(57) ABSTRACT

The invention pertains to a formulation comprising magnetic nanoparticles (MENPs) conjugated to or mixed with a therapeutic cargo, the therapeutic cargo comprising an HIV inhibitor, an inhibitor of BACE-1 activity or expression, and a cocaine antagonist. In one embodiment, the formulation comprises WA, miR-107, and BD1063. The MENPs conjugated or mixed with the therapeutic cargo can be encapsulated within liposomes. The liposomes can be surface modified with an affinity ligand that targets the liposomes to the brain. The invention also pertains to a method of treating an HIV infection in a subject having cocaine addiction, by administering to the subject the formulation of the invention and applying to the subject magnetic forces to guide the MENPs across the blood brain barrier and into brain parenchyma and releasing the therapeutic cargo into the brain parenchyma by applying to the subject an alternating current.

20 Claims, 8 Drawing Sheets
Specification includes a Sequence Listing.

(56) References Cited

OTHER PUBLICATIONS

H Ding, V Sagar, M Agudelo, S Pilakka-Kanthikeel, VSR Atluri, A Raymond, T Samikkannu, MP Nair. "Enhanced blood—brain barrier transmigration using a novel transferrin embedded fluorescent magnetoliposome nanoformulation." Nanotechnology, vol. 25, pp. 1-14. (Year: 2014).*
HS Toh, RG Compton. "Electrochemical detection of single micelles through 'nano-impacts." Chemical Science, vol. 6, 2015, pp. 5053-5058. (Year: 2015).*
JN Israelachvili, S Marcelja, RG Horn. "Physical principles of membrane organization." Quarterly Reviews of Biophysics, vol. 13(2), 1980, pp. 121-200. (Year: 1980).*
Court of Appeals of the Federal Circuit. Pozen Inc. v. Par Pharmaceutical Inc. 696 F.3d 1151 (2012). https://scholar.google.com/scholar_case?case=13936289819142989723&hl=en&as_sdt=6&as_vis=1&oi=scholarr accessed Sep. 13, 2018, originally published 2012, 15 printed pages. (Year: 2012).*
Achim, C.L. et al., "Increased Accumulation of Intraneuronal Amyloid β in HIV-Infected Patients." J. Neuroimmune Pharmacol., Jun. 2009, 4(2):190-199, doi: 10.1007/s11481-009-9152-8.
Adle-Biassette, H. etal., "Neuronal Apoptosis Does Not Correlate with Dementia in HIV Infection but is Related to Microglial Activation and Axonal Damage." Neuropathology and Applied Neurobiology, Apr. 1999, 25(2):123-133, doi: 10.1046/j.1365-2990.1999.00167.x.
Antinori, A. et al., "Updated Research Nosology for HIV-Associated Neurocognitive Disorders." Neurology, Oct. 2007, 69(18):1789-99, doi: 10.1212/01.WNL.0000287431.88658.8b.
Antunes, M., Biala, G. "The Novel Object Recognition Memory: Neurobiology, Test Procedure, and its Modifications." Cognitive Processing, May 2012, 13(2):93-110, doi: 10.1007/s10339-011-0430-z.
Bertrand, L. et al., "Antiretroviral Treatment with Efavirenz Disrupts the Blood-Brain Barrier Integrity and Increases Stroke Severity." Scientific Reports, Dec. 2017, e:39738, doi: 10.1038/srep39738.
Bertrand, L. et al., "Induction of Ischemic Stroke and Ischemia-Reperfusion in Mice Using the Middle Artery Occlusion Technique and Visualization of Infarct Area." J. Vis. Exp., Feb. 2017, 2(120):Abstract.
Bhardwaj, V. et al., "Efficient Intracellular Delivery and Improved Biocompatibility of Colloidal Silver Nanoparticles Towards Intracellular SERS Immuno-Sensing." Analyst, Apr. 2015, 140:3929-3934, doi: 10.1039/c5an00435g.
Buch, S. et al., "Cocaine and HIV-1 Interplay in CNS: Cellular and Molecular Mechanisms." Curr HIV Res, Jul. 2012, 10(5):425-428.
Carrera, I. et al., "Vaccine Development to Treat Alzheimer's Disease Neuropathology in APP/PS1 Transgenic Mice." Int. J. Alzheimers Dis., Jun. 2012, 2012:1-17, doi: 10.1155/2012/376138.
Das, T.K. et al., "Potential of Glycowithanolides from Withania Somnifera (Ashwagandha) as Therapeutic Agents for the Treatment of Alzheimer's Disease." World Journal of Pharmaceutical Research, May 2015, 4(6):16-38.
Davis, L.E. et al., Early Viral Brain Invasion in Iatrogenic Human Immunodeficiency Virus Infection. Neurology, Sep. 1992, 42(9):Abstract.
Dickson, D.W. et al., "Central Nervous System Pathology in Pediatric AIDS." Ann. N. Y. Acad. Sci., 1993, 693:93-106.
Ding, H. et al., "Enhanced Blood-Brain Barrier Transmigration Using a Novel Transferrin-Embedded Fluorescent Magneto Liposome Nanoformulation." Nanotechnology, Feb. 2014, 25(5):1-30, doi: 10.1088/0957-4484/25/5/055101.
Esiri, M.M. et al., "Prevalence of Alzheimer Plaques in Aids." J. Neurol. Neurosurg. Psychiatry, Jul. 1998, 65(1):29-33.
Fiala, M. etal., "Cocaine Enhances Monocyte Migration Across the Blood-Brain Barrier. Cocaine's Connection to AIDS Dementia and Vasculitis?" Adv Exp Med Biol, 1998, 437:Abstract.
Gandhi, N. et al., "Interactive Role of Human Immunodeficiency Virus Type 1 (HIV-1) Clade-Specific Tat Protein and Cocaine in Blood-Brain Barrier Dysfunction: Implications for HIV-1-Associated Neurocognitive Disorder." J. Neurovirol., Jul. 2010, 16(4):294-305, doi: 10.3109/13550284.2010.499891.
Gannon, P. et al., "Current Understanding of HIV-Associated Neurocognitive Disorders Pathogenesis." Curr. Opin. Neurol., Jun. 2011, 24(3):275-83, doi: 10.1097/WCO.0b013e32834695fb.
Giometto, B. etal., "Accumulation of Beta-Amyloid Precursor Protein in HIV Encephalitis: Relationship with Neuropsychological Abnormalities." Ann. Neurol., Jul. 1997, 42(1):Abstract.
Giunta, B. et al., "Antiretroviral Medications Disrupt Microglial Phagocytosis of β-Amyloid and Increase its Production by Neurons: Implications for HIV-Associated Neurocognitive Disorders." Molecular Brain, Jun. 2011, 4: 23, doi: 10.1186/1756-6606-4-23.
Green, D.A. et al., "Brain Deposition of Beta-Amyloid is a Common Pathologic Feature in HIV Positive Patients." AIDS, Mar. 2005, 19(4):407-411.
Guduru, R. et al., "Magneto-electric Nanoparticles to Enable Field-controlled High-Specificity Drug Delivery to Eradicate Ovarian Cancer Cells." Nature Scientific Reports, Oct. 2013, 3(2953):1-8, doi: 10.1038/srep02953.
Hadas, E. et al., "Transmission of Chimeric HIV by Mating in Conventional Mice: Prevention by Pre-Exposure Antiretroviral Therapy and Reduced Susceptibility During Estrus." Dis. Model. Mech., Sep. 2013, 6(5):1292-1298, doi: 10.1242/dmm.012617.
Halima, S.B. et al., "Specific Inhibition of β-Secretase Processing of the Alzheimer Disease Amyloid Precursor Protein." Cell Reports, Mar. 2016, 14(9):2127-2141, doi: 10.1016/j.celrep.2016.01.076.
Hayashi, K. et al., "HIV-TAT Protein Upregulates Expression of Multidrug Resistance Protein 1 in the Blood-Brain Barrier." J. Cereb. Blood Flow Metab., Aug. 2006, 26(8):1052-1065, doi: 10.1038/sj.jcbfm.9600254.
He, H. et al., "Enhanced Human Immunodeficiency Virus Type 1 Expression and Neuropathogenesis in Knockout Mice Lacking Type I Interferon Responses." J. Neuropathol. Exp. Neurol., Jan. 2014, 73(1):59-71, doi: 10.1097/NEN.0000000000000026.
Horger, B.A. et al.., "Enhancement of Locomotor Activity and Conditioned Reward to Cocaine by Brain-Derived Neurotrophic Factor." J. Neurosci., May 1999, 19(10):4110-4122.
Husebekk, A. et al., "Serum Amyloid Protein A (SAA): An Indicator of Inflammation in AIDS and AIDS-Related Complex (ARC)." Scand J Infect Dis, 1986, 18(5):Abstract.
Jayant, R.D. et al., "Sustained-release nanoART Formulation for the Treatment of neuroAIDS." International Journal of Nanomedicine, Feb. 2015, 10:1077-1093, doi: 10.2147/IJN.S76517.
Jones, L.D. et al.,"Modeling HIV-1 Induced Neuroinflammation in Mice: Role of Platelets in Mediating Blood-Brain Barrier Dysfunction." PLOS ONE, Mar. 2016, 11(3):1-26, doi: 10.1371/journal.pone.0151702.
Kaushik, A. et al., "Magnetically Guided Central Nervous System Delivery and Toxicity Evaluation of Magneto-Electric Nanocarriers." Sci. Rep., May 2016, 6(25309):1-10, doi: 10.1038/srep25309.
Kelschenbach, J.L. et al., "Mice Chronically Infected with Chimeric HIV Resist Peripheral and Brain Superinfection: A Model of Protective Immunity to HIV." J. Neuroimmune Pharmacol., Jun. 2012, 7(2):380-387, doi: 10.1007/s11481-011-9316-1.
Kurapati, K.R.V. et al., "Ashwagandha (Withania somnifera) Reverses β-Amyloid$_{1-42}$ Induced Toxicity in Human Neuronal Cells: Implications in HIV-Associated Neurocognitive Disorders (HAND)." PLOS One, Oct. 2013, 8(1):1-15, doi: 10.1371/journal.pone.0077624.
Kurapati, K.R.V. et al., "Ashwagandha (Withania somnifera) Reverses HIV-1 Induced Neurodegeneration via Attenuation of (β-Amyloid plaques: Implications in HIV-Associated Neurocognitive Disorders (HAND)." Society on NeuroImmune Pharmacology, Mar. 2014, p:58:Abstract.
Kurapati, K.R.V. et al., "β-Amyioid$_{1-42}$, HIV-1$_{Ba-L}$ (Clade B) Infection and Drugs of Abuse Induced Degeneration in Human Neuronal Cells and Protective Effects of Ashwagandha (Withania somnifera) and Its Constituent Withanolide A." PLOS One, Nov. 2014, 9(11):1-23, doi: 10.1371/journal.pone.0112818.

(56) References Cited

OTHER PUBLICATIONS

Lackner, A.A. et al., "Early Events in Tissues During Infection With Pathogenic (SIVmac239) and Nonpathogenic (SIVmac1A11) Molecular Clones of Simian Immunodeficiency Virus." *Am. J. Pathol.*, Aug. 1994, 145(2):428-439.
Li, S. et al., "Matrix Metalloproteinase Levels in Early HIV Infection and Relation to in Vivo Brain Status." J. Neurovirol., Oct. 2013, 19(5):452-460, doi: 10.1007/s13365-013-0197-3.
Liu, S.J. et al., "Alzheimer-like Phosphorylation of Tau and Neurofilament Induced by Cocaine in vivo[1]." *Acta. Pharmacol. Sin.*, Jun. 2003, 24(6):512-518.
Liu, Y., Matsumoto, R.R., "Alterations in Fos-Related Antigen 2 and $o_1$ Receptor Gene and Protein Expression are Associated with the Development of Cocaine-Induced Behavioral Sensitization: Time Course and Regional Distribution Studies." *J. Pharmacol. Exp. Ther.*, Jun. 2008, 327(1):187-195, doi: 10.1124/jpet.108.141051.
Liu, Y. et al., "Cocaine Up-Regulates Fra-2 and σ-1 Receptor Gene and Protein Expression in Brain Regions Involved in Addiction and Reward." *J. Pharmacol. Exp. Ther.*, May 2005, 314(2):770-779, doi: 10.1124/jpet.105.084525.
Maragos, W.F. et al., "Neuronal Injury in Hippocampus with Human Immunodeficiency Virus Transactivating Protein, TAT." *Neuroscience*, Mar. 2003, 117(1):43-53, doi: 10.1016/S0306-4522(02)00713-3.
Matsumoto, R.R. et al., "Conformationally Restricted Analogs of BD1008 and an Antisense Oligodeoxynucleotide Targeting $\sigma_1$ Receptors Produce Anti-Cocaine Effects in Mice." *Eur. J. Pharmacol.*, Apr. 2001, 419(2-3):163-174, doi: 10.1016/S0014-2999(01)00968-2.
McArthur, J.C. et al., "HIV-Associated Neurocognitive Disorders: Is There a Hidden Epidemic?" *AIDS*, Feb. 2010, 24(9):1367-1370, doi: 10.1097/QAD.0b013e3283391d56.
Mirjalili, M.H. et al., "Steroidal Lactones from *Withania Somnifera*, an Ancient Plant for Novel Medicine." *Molecules*, Jul. 2009, 14(7):2373-2393, doi: 10.3390/molecules14072373.
Mishra, L.C. et al., "Scientific Basis for the Therapeutic Use of *Withania Somnifera* (Ashwagandha): A Review." *Altern. Med. Rev.*, Aug. 2000, 5(4):334-346.
Mohan, R. et al., "Withaferin A is a Potent Inhibitor of Angiogenesis." *Angiogenesis*, May 2004, 7(2):115-22, doi: 10.1007/s10456-004-1026-3.
Moidunny, S. et al., "Oncostatin M Promotes Excitotoxicity by Inhibiting Glutamate Uptake in Astrocytes: Implications in HIV-Associated Neurotoxicity." *J. Neuroinflammation.*, Jun. 2016, 13(1):1-18, doi: 10.1186/s12974-016-0613-8.
Nair, M. et al., "Externally Controlled On-Demand Release of Anti-HIV Drug Using Magneto-Electric Nanoparticles as Carriers." *Nature Communications*, Apr. 2013, 4:1-7, doi: 10.1038/ncomms2717.
Nair, M. et al., "Getting Into the Brain: Potential of Nanotechnology in the Management of Neuroaids." *Adv. Drug Deliv. Rev.*, Mar. 2016, 103:202-217, doi: 10.1016/j.addr.2016.02.008.
Nelson, P.T., Wang, W-X., "MiR-107 is Reduced in Alzheimer's Disease Brain Neocortex: Validation Study." *Journal of Alzheimer's Disease*, Jan. 2010, 21(1):75-79, doi: 10.3233/JAD-2010-091603.
Patil, D. et al., "Determination of Withaferin A and Withanolide A in Mice Plasma Using High-Performance Liquid Chromatography-Tandem Mass Spectrometry: Application to Pharmacokinetics After Oral Administration of *Withania Somnifera* Aqueous Extract." *Journal of Pharmaceutical and Biomedical Analysis*, Mar. 2013, 80:203-212, doi: 10.1016/j.jpba.2013.03.001.
Peluso, M.J. et al., "Cerebrospinal Fluid and Neuroimaging Biomarker Abnormalities Suggest Early Neurological Injury in a Subset of Individuals During Primary HIV Infection." *J. Infect. Dis.*, Jun. 2013, 207(11): 1703-1712, doi: 10.1093/infdis/jit088.
Persidsky, Y. et al., "A Model for Monocyte Migration Through the Blood-Brain Barrier During HIV-1 Encephalitis." *The Journal of Immunology*, Apr. 1997, 158(7):3499-3510.
Potash, M.J. et al., "A Mouse Model for Study of Systemic HIV-1 Infection, Antiviral Immune Responses, and Neuroinvasiveness." *Proc. Natl. Acad. Sci. USA*, Jan. 2005, 102(10):3760-3765, doi: 10.1073/pnas.0500649102.
Pu, H. et al., "HIV-1 Tat Protein-Induced Alteration of ZO-1 Expression are Mediated by Redox-Regulated ERK 1/2 Activation." *J. Cereb. Blood Flow Metab.*, Apr. 2005, 25(10):132516-35, doi: 10.1038/sj.jcbfm.9600125.
Pu, H. et al., "HIV-1 Tat Protein Upregulates Inflammatory Mediators and Induces Monocyte Invasion into the Brain." *Molecular and Cellular Neuroscience*, May 2003, 24(1):224-237, doi: 10.1016/S1044-7431(03)00171-4.
Radde, R. et al., "Aβ42-Driven Cerebral Amyloidosis in Transgenic Mice Reveals Early and Robust Pathology." *EMBO Rep.*, Aug. 2006, 7(9):940-946, doi: 10.1038/sj.embor.7400784.
Rempel, H.C., Pulliam, L., "HIV-1 Tat Inhibits Neprilysin and Elevates Amyloid β." *AIDS*, Jan. 2005, 19(2):127-35.
Reynolds, J.L. et al., "Proteomic Analysis of the Effects of Cocaine on the Enhancement of HIV-1 Replication in Normal Human Astrocytes (NHA)." *Brain Res.*, Dec. 2006, 1123(1):226-236, doi: 10.1016/j.brainres.2006.09.034.
Sagar, V. et al., "Towards Nanomedicines for neuro-AIDS." *Rev. Med. Virol.*, Mar. 2014, 24(2):103-124, doi: 10.1002/rmv.1778.
Saiyed, Z.M. et al., "Magnetic Nanoformulation of Azidothymidine 5'-Triphosphate for Targeted Delivery Across the Blood-Brain Barrier." *International Journal of Nanomedicine*, Mar. 2010, 5:157-166, doi: 10.2147/IJN.S8905.
Samikkannu, T. et al., "HIV and Cocaine Impact Glial Metabolism: Energy Sensor AMP-activated Protein Kinase Role in Mitochondrial Biogenesis and Epigenetic Remodeling." *Sci. Rep.*, Aug. 2016, 6:1-11, doi: 10.1038/srep31784.
Shi, T. et al., "Nf-κb-Dependent Inhibition of HIV-1 Transcription by Withaferin A." *HIV Curr. Res.*, Nov. 2016, 1(3):1-6.
Soontornniyomkij, V. et al., "Cerebral β-amyloid deposition predicts HIV-associated neurocognitive disorders in APOE ε4 carriers." *AIDS*, Nov. 2012, 26(18):2327-2335, doi: 10.1097/QAD.0b013e32835a117c.
Stephens, E.B. et al., "The Primary Phase of Infection by Pathogenic Simian-Human Immunodeficiency Virus Results in Disruption of the Blood-Brain Barrier." *AIDS Res. Hum. Retroviruses*, Oct. 2003, 19(10): 837-846, doi: 10.1089/088922203322493003.
Tatro, E.T. et al., "Evidence for Alteration of Gene Regulatory Networks Through MicroRNAs of the HIV-Infected Brain: Novel Analysis of Retrospective Cases." *PLOS ONE*, Apr. 2010, 5(4):1-13, doi: 10.1371/journal.pone.0010337.
Tremblay, M.E. et al, Preparation of Mouse Brain Tissue for Immunoelectron Microscopy. *Journal of Visualized Experiments: JoVE*, Jul. 2010, (41):1-5, doi: 10.3791/2021.
Wang, W.-X., et al., The Expression of MicroRNA miR-107 Decreases Early in Alzheimer's Disease and May Accelerate Disease Progression through Regulation of β-Site Amyloid Precursor Protein-Cleaving Enzyme 1. *The Journal of Neuroscience*, Jan. 2008, 28(5):1-27, doi: 10.1523/JNEUROSC1.5065-07.2008.
Winters, M., "Ancient Medicine, Modern Use: *Withania Somnifera* and its Potential Role in Integrative Oncology." *Altern. Med. Rev.*, Dec. 2006, 11(4):269-77.
Wright, P.W. et al., "Cerebral White Matter Integrity During Primary HIV Infection." *AIDS*, Feb. 2015, 29(4):1-17, doi: 10.1097/QAD.0000000000000560.
Yelamanchili, S.V. et al., "Microrna-21 Dysregulates the Expression of MEF2C in Neurons in Monkey and Human SIV/HIV Neurological Disease." *Cell Death Dis.*, 2010. 1:1-11, doi: 10.1038/cddis.2010.56.

\* cited by examiner

Control

HIV

HIV+WA

Overlap

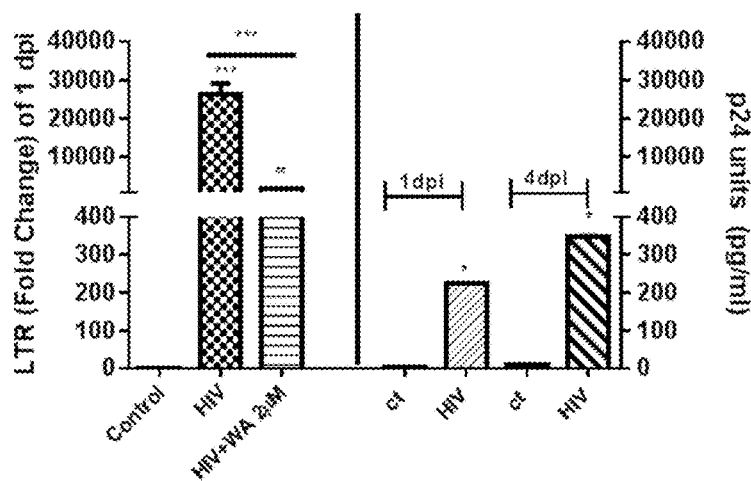
FIG. 8A    FIG. 8B
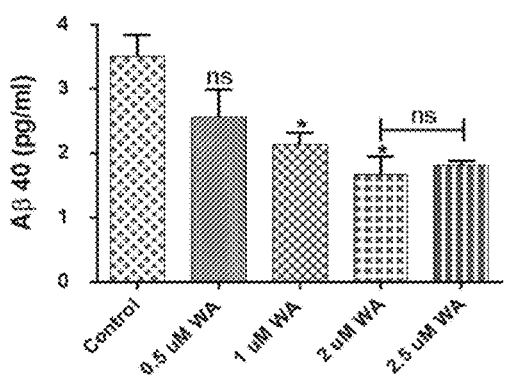    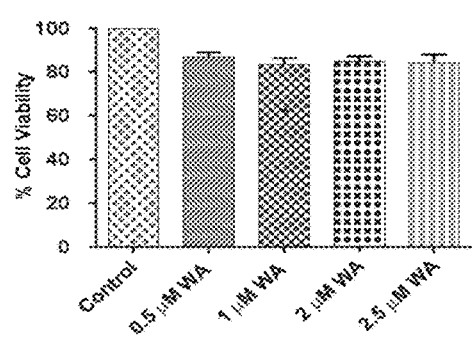
FIG. 9A    FIG. 9B

SEQUENCE LISTING

```
<160> NUMBER OF SEQ ID NOS: 2

<210> SEQ ID NO 1
<211> LENGTH: 81
<212> TYPE: RNA
<213> ORGANISM: Homo sapiens

<400> SEQUENCE: 1
cucucugcuu ucagcuucuu uacaguguug ccuuguggca uggaguucaa gcagcauugu     60
acagggcuau caaagcacag a                                              81

<210> SEQ ID NO 2
<211> LENGTH: 23
<212> TYPE: RNA
<213> ORGANISM: Homo sapiens

<400> SEQUENCE: 2
agcagcauug uacagggcua uca                                            23
```

COMPOSITIONS AND METHODS FOR TREATING HIV-ASSOCIATED NEUROCOGNITIVE DISORDERS

GOVERNMENT SUPPORT

This invention was made with government support under RO1-DA040537, RO1-DA037838, and RO1-DA042706-A awarded by National Institute of Health. The government has certain rights in the invention.

The Sequence Listing for this application is labeled "SeqList-17Feb17-ST25," which was created on Feb. 17, 2017, and is 1 KB. The Sequence Listing is incorporated herein by reference in its entirety.

BACKGROUND OF THE INVENTION

With proper medications human immunodeficiency virus (HIV) patients now live almost full lifespans; however, HIV associated neurocognitive disorder (HAND) continues and its prevalence is increasing. This may be, in part, because HIV infection remains in the brain.

HAND is characterized by the development of cognitive, behavioral and motor abnormalities. HAND comprises a progressive pattern of CNS involvement that ranges from asymptomatic neurocognitive impairment (ANI) and minor neurocognitive disorder (MND), to the most severe HIV-associated dementia (HAD). HIV infection in the brain also leads to increased Alzheimer amyloid precursor protein (AβPP) production and susceptibility to amyloid beta (Aβ) deposition, which may induce the development of HAND. Anti-retroviral therapies (ARV) have been shown to improve cognition and reduce the prevalence of HIV-associated dementia; however, continued HIV infection and aging process exacerbate the incidence of HAND.

Role of α, β, and γ-secretases in amyloidogenesis: Deposition of extracellular Aβ plaques and intracellular Aβ and Tau neurofibrillary tangles (NFTs) are major pathological hallmarks of neurocognitive dysfunctions. Intraneuronal accumulations of Aβ and increased formation of insoluble Aβ plaques in brain continue to be implicated in the pathogenesis of various neurological disorders including Alzheimer's disease (AD) and HAND. Increased amyloidogenic metabolism of AβPP by α-secretase and γ-secretase results in the formation of soluble AβPP (sAPP), which plays a protective role in normal synaptic signaling, learning, memory, emotional behaviors, and neuronal survival. However, AβPPP can be also cleaved sequentially by β-secretase and γ-secretase to release the Aβ1-40 and Aβ1-42 which can aggregate to form plaques. Neurofibrillary tangles (NFTs), the hallmark of neurocognitive dysfunctions, are principally composed of abnormally phosphorylated Tau protein.

Recent decades have witnessed an entangled epidemic of cocaine abuse and HIV infection. Cocaine enhances the replication of HIV-1, suggesting a link between cocaine use and progression of HIV-1 infection. Cocaine also exacerbates the effect of HIV in the brain. These hypotheses are supported by a number of clinical studies, animal models, and in vitro investigations. Although clinical studies report associations between HIV and cocaine, the underlying molecular mechanisms of cocaine-induced effects in HAND remain unclear. Husebekk et al. reported elevated levels of acute phase level of serum amyloid protein A (a precursor to amyloid fibrils) in male homosexuals with acquired immune deficiency syndrome (AIDS) or AIDS-related complex. Giometto et al. reported the accumulation of Aβ precursor protein in HIV encephalitis brains. Increased prevalence of amyloid plaques was also reported in the cortex of AIDS brains compared with age-matched, non-HIV-infected controls. Subsequently, studies showed increased amyloid deposition in the brains of HIV-1-infected patients. Studies also suggest that an HIV-1 infection in the brain facilitates Aβ deposition and amyloid plaque formation which may induce the development of HAND. Liu et al. reported that peritoneal injection of cocaine in rats stimulated hyperphosphorylation of tau and neurofilament in cortex, hippocampus and caudato-putamen regions of brain.

As such, neurocognitive dysfunction is enhanced in HIV patients that are ingesting cocaine and other drugs of abuse. Cocaine causes neuronal impairments as well as increases the incidence and severity of HAND. Despite significant therapeutic advances made in the management of HIV, effective treatments against HIV infection in the brain and the pathogenesis of HAND remains a formidable task. This may be partly because of the lack of understanding of the underlying mechanisms and partly because of the inability of drugs to cross the blood brain barrier (BBB). In addition, neurological complications associated with HIV have changed over the past 30 years; clinical and pathological features of HAND have become more like Alzheimer's disease including the presence of increased brain deposition of amyloid-β (Aβ) proteins.

BRIEF SUMMARY OF THE INVENTION

The invention provides novel therapeutic interventions against HAND, particularly, in HIV patients using cocaine. The compositions and methods described herein are based on bi-functional plant molecule, Withaferin-A (WA), that can eradicate HIV and remove neuronal amyloid beta (Aβ) protein. Certain embodiments of the invention provide a formulation comprising magnetic nanoparticles (MENPs) conjugated to or mixed with a therapeutic cargo, the therapeutic cargo comprising an HIV inhibitor, an inhibitor of beta-secretase 1 (BACE-1) activity or expression, and a cocaine antagonist. In one embodiment, the formulation comprises WA, microRNA 107 (miR-107), and 1-[2-(3,4-Dichlorophenyl)ethyl]-4-methylpiperazine dihydrochloride (BD1063).

The MENPs conjugated or mixed with the therapeutic cargo can be encapsulated within liposomes. In one embodiment, the liposomes are surface modified with an affinity ligand that targets the liposomes to the brain.

The invention also provides a method of treating an HIV infection in a subject having cocaine addiction by administering to the subject the formulation of the invention and applying to the subject magnetic forces to guide the MENPs across the BBB and into brain parenchyma. The therapeutic cargo is released into the brain parenchyma by applying to the subject an alternating current.

BRIEF DESCRIPTION OF THE FIGURES

FIGS. 8A-8B show that HIV infects SH-APP cells and WA suppresses HIV: (A): LTR detection after 1 dpi (days post infection) of HIV infection (i) HIV (100 ng) and (ii) HIV (100 ng) and WA (2 µM); (B) p24 ELISA for SH-APP HIV exposed up to 1 and 4 dpi. (n=3; *, p≤0.05; , p≤0.01; and *, p≤0.001.)

FIGS. 9A-9B show Aβ1-40 ELISA of WA treated SHAPP cells: Dose response studies shows that 2 mM WA significantly attenuates β-Amyloid production (A). Cell viability study in SH-APP cells: MTT cytotoxicity assay demonstrates that no significant cytotoxicity of WA was observed after 48 hours of treatment. (n=3; *, p≤0.05; NS-Not Significant).

BRIEF DESCRIPTION OF SEQUENCES

Figure 1A:
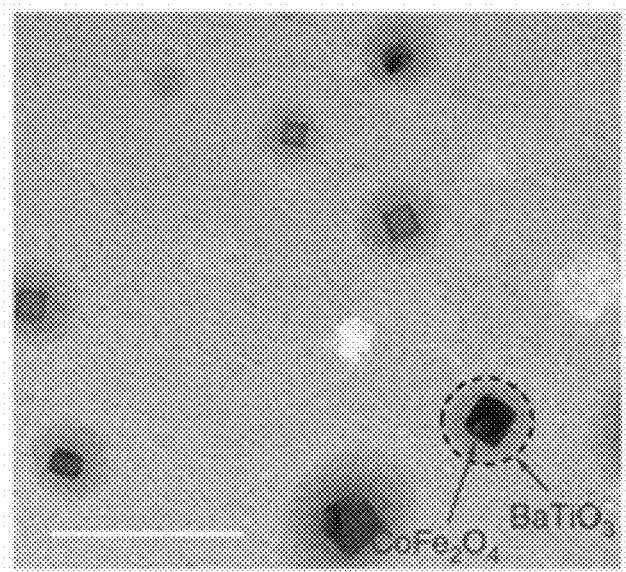
FIGS. 1A-1B provide (A) TEM image of MENPs: Image show the core-shell structure of a MENPs, Scale bar-100 nm and (B) Energy-dispersive spectroscopy (EDS) analysis of MENPs for the confirmation elemental analysis.

SEQ ID NO: 1: Pre-miRNA sequence for miR107
SEQ ID NO: 2: Mature miRNA sequence for miR107:

DETAILED DESCRIPTION OF THE INVENTION

Several factors contribute to development and acceleration of HAND in HIV infected patients that are addicted to cocaine. The invention pertains to compositions and methods that are designed to target several points of interest in regulation and progression of HAND.

WA (CAS number: 5119-48-2,5,6-Epoxy-4,27-dihydroxy-1-oxowitha-2,24-dienolide), is extracted from *Withania somnifera*. WA has potent anti-inflammatory properties as it inhibits the activation of nuclear factor-κB (NF-κB) signaling pathway. WA inhibited HIV replication in microglial cells and neuroblastoma cells, and significantly reduced Aβ formation in AβPP-transfected SH-SY5Y neural cells. Also, WA reversed HIV induced increases in Aβ formation in AβPPP transfected cells.

MicroRNAs (miR) are small non-coding RNAs involved in post-transcriptional regulation of gene expression. Dysfunctional miRNA regulation has been shown to contribute to the neuropathology of HAND and miRNA profiling data shows that miR-107 is significantly altered in HAND and other neurological disorders. A reciprocal relationship is demonstrated between the levels of miR-107 and β-secretase. miR-107 is consistently associated with increased amyloidogenesis including upregulation of the rate limiting enzyme β-secretase (BACE-1). Early decrease in miR-107 with a concomitant increase in β-secretase mRNA levels and activity has been reported in AD and other neurological disorders. The invention demonstrates that miR107 binds to the MENPs by electrostatic binding and can be released from MENP by alternating current in a controlled fashion (FIG. 2).

Sigma receptors ($\sigma_1$ & $\sigma_2$) are protein targets for cocaine and are involved in the toxic and stimulant actions of cocaine. Cocaine antagonists, for example, $\sigma_1$ and $\sigma_2$ receptor antagonists, block behavioral effects of cocaine. BD1063 dihydrochioride (σ-1 receptor specific antagonist) has been shown to overcome deleterious effects of cocaine. Pretreatment of mice with BD1063 significantly attenuated cocaine-induced convulsions and locomotor stimulatory effects. However, BD1063 does not cross BBB.

Nanotechnology and MENPs are used for temporally controlled and site specific release of drugs/miRNA across the BBB. Nanotechnology can be employed to carry out multiple specific functions at once or in a predefined sequence, an important requirement for the clinically successful delivery of drugs and other molecules to the CNS. Nanotechnology-based approaches to targeted delivery of drugs and other molecules/proteins across the BBB can be engineered to perform specific functions as needed. Drug loaded magnetized monocytes, magnetic nanoparticles (MNP) loaded with anti-HIV drugs, latency breaking agents, neuroprotecting agents and drugs of abuse antagonists can be transmigrated across the BBB on application of external magnetic force without affecting the integrity of the BBB. As such, nanotechnology can be used for developing novel drug delivery systems to the brain which is a main target organ for HIV and cocaine.

United State Patent Application Publications US20130317279, US20110213193, US20150283368, and US20160030724 describe MENPs as novel drug carriers that offer a unique capability of low energy and dissipation-free on-demand drug release across the BBB. The nanoparticles described in US20130317279, US20110213193, US20150283368, and US20160030724 have magnetic and electrical properties that can be used to deliver drugs across BBB on application of external magnetic field and controlled drug release via application of electrical forces without inducing heat. US20130317279, US20110213193, US20150283368, and US20160030724 are incorporated by reference in their entirety.

An embodiment of the invention provides a formulation comprising MENPs conjugated to or mixed with a therapeutic cargo, the therapeutic cargo comprising an HIV inhibitor, an inhibitor of BACE-1 activity or expression, and a cocaine antagonist. The formulation of the invention can be used to deliver the therapeutic cargo across the BBB via the application of noninvasive external magnetic force and/or alternating current that releases the drugs in a controlled manner. Once the therapeutic cargo is delivered to the brain, different components of the therapeutic cargo act on different aspects of HAND, for example, reducing HIV infection, reducing β-secretase levels and activity, and reducing cocaine-induced neuronal dysfunctions, Tau phosphorylation, Aβ deposition. As such, the formulation described herein can be used to treat HAND in HIV patients, particularly, HIV patients addicted to cocaine.

A number of HIV inhibitors are known in the art and can be divided into nucleoside-analog reverse transcriptase inhibitors (NNRTIs), non-nucleoside reverse transcriptase inhibitors (NNRTIs), integrase inhibitors, protease inhibitors, fusion inhibitors, and co-receptor antagonists. Non-limiting examples of HIV inhibitors include: abacavir sulfate, didanosine (delayed-release didanosine, dideoxyinosine, enteric-coated didanosine, ddI, ddI EC), emtricitabine, lamivudine, stavudine, tenofovir disoproxil fumarate, zidovudine (azidothymidine), efavirenz, etravirine, nevirapine (extended-release nevirapine, NVP), rilpivirine (rilpivirine hydrochloride, RPV), atazanavir (atazanavir sulfate), darunavir (darunavir ethanolate), fosamprenavir (fosamprenavir calcium), indinavir (indinavir sulfate), nelfinavir (nelfinavir mesylate), ritonavir, saquinavir (saquinavir mesylate), tipranavir, enfuvirtide, maraviroc, dolutegravir, elvitegravir, raltegravir (raltegravir potassium). In a particular embodiment, the HIV inhibitor is an inhibitor of HIV transcription, for example, WA. In further embodiments, a pharmacokinetic enhancer, for example, cobicistat, is included in the therapeutic cargo.

In certain embodiments, a combination of HIV inhibitors is used. Non-limiting examples of the combinations of HIV inhibitors include:
 abacavir and lamivudine
 abacavir, dolutegravir, and lamivudine
 abacavir, lamivudine, and zidovudine
 atazanavir and cobicistat
 darunavir and cobicistat
 efavirenz, emtricitabine, and tenofovir disoproxil fumarate
 elvitegravir, cobicistat, emtricitabine, and tenofovir alafenamide fumarate
 elvitegravir, cobicistat, emtricitabine, and tenofovir disoproxil fumarate
 emtricitabine, rilpivirine, and tenofovir alafenamide
 emtricitabine, rilpivirine, and tenofovir disoproxil fumarate
 emtricitabine and tenofovir alafenamide
 emtricitabine and tenofovir disoproxil fumarate
 lamivudine and zidovudine
 lopinavir and ritonavir Additional examples of HIV inhibitors or combinations of HIV inhibitors are known to a skilled artisan and such embodiments are within the purview of the invention.

A number of BACE-1 inhibitors are known in the art. BACE-1 inhibitors can inhibit expression or activity of BACE-1. In one embodiment, BACE-1 inhibitor is an inhibitor polynucleotide that inhibits the expression of BACE-1 mRNA. Such inhibitory polynucleotide can be an antisense polynucleotide, shRNA, siRNA, or miRNA. In one embodiment, the miRNA is miR-107.

A person of ordinary skill in the art can design an appropriate antisense RNA, shRNA, siRNA, or miRNA against BACE-1 mRNA and such embodiments are within the purview of the invention. miR-107 can be a primary miR-107, pre-miR-107, or mature miR-107. miR-107 can consist of primary miR-107, pre-miR-107, or mature miR-107 sequence or can be in the form of an expression vector that encodes the primary miR-107, pre-miR-107, or mature miR-107 upon entry into the cells of the subject. Various techniques of preparing vectors expressing an oligonucleotide or miRNA are well known to a person of ordinary skill in the art and such embodiments are within the purview of the invention.

In one embodiment, the BACE-1 inhibitor is a small molecule compound. A small molecule compound is a compound having a low molecular weight, particularly, a molecular weight of less than about 1000 daltons.

Non-limiting examples of BACE-1 inhibitors include: AZD3293 (4-Methoxy-5"-methyl-6'-[5-(prop-1-yn-1-yl)pyridin-3-yl]-3'H-dispiro[cyclohexane-1,2'-indene-1',2"-imidazole]-4"-amine), CTS-21166, E2609, HPP854, LY2886721 (N-[3-[(4aS,7aS)-2-amino-4,4a,5,7-tetrahydrofuro[3,4-d][1,3]thiazin-7a-yl]-4-fluorophenyl]-5-fluoropyridine-2-carboxamide), MK-8931 (N-[3-[(5R)-3-amino-5,6-dihydro-2,5-dimethyl-1,1-dioxido-2H-1,2,4-thiadiazin-5-yl]-4-fluorophenyl]-5-fluoro-2-pyridinecarboxamide), PF-05297909, RG7129, TAK-070 (N,N-dimethyl-2-[(2R)-6-[(4-phenylphenyl)methoxy]-1,2,3,4-tetrahydronaphthalen-2-yl]ethanamine), or VTP-37948.

Additional examples of BACE-1 inhibitors are known and such embodiments are within the purview of the invention.

A number of cocaine antagonists are known in the art. Non-limiting examples of cocaine antagonists include AHN2-005 (N-allyl-3α-[bis(4'-fluorophenyl)methoxy]-tropane; JHW 007 (N-(n-butyl)-3α-[bis-(4'-fluorophenyl)methoxy]-tropane); Rimcazole, 9-[3-(cis-3,5-dimethyl-1-piperazinyl)propyl]-9H-carbazole; SH 3-24 ([3-(cis-3,5-dimethyl-4-[3-phenylpropyl]-1-piperazinyl)-propyl] diphenylamine); SH 3-28 (9-[3-(cis-3,5-dimethyl-4-[3-phenylpropyl]-1-piperazinyl)-propyl]carbazole); GBR 12909 (1-(2-[bis(4-fluorophenyl)methoxy]ethyl)-4-(3-phenylpropyl)piperazine; methylphenidate; nomifensine; RTI-366 (3β-(4-chlorophenyl)-2β-[3-(4-methylphenyl)isoxazol-5-yl]tropane); WIN 35,428 ((−)-3β-(4-fluorophenyl)-tropan-2β-carboxylic acid methyl ester tartrate). In one embodiment, a cocaine antagonist is BD1063 (1-[2-(3,4-Dichlorophenyl)ethyl]-4-methylpiperazine). Additional examples of cocaine antagonists are known in the art and such embodiments are within the purview of the invention.

One embodiment of the invention provides a nanoparticle formulation containing a therapeutic cargo comprising WA, miR-107; and BD1063. Certain nanoparticle formulations of the subject invention contain MENPs conjugated with the combination of WA, miR-107, and BD1063. In one embodiment, nanoparticle formulations contain MENPs described in US20130317279, US20110213193, US20150283368, and US20160030724. In a further embodiment, MENPs are encapsulated into liposomes, optionally, further modified to target the MENPs to specific cells, for example, brain cells.

MENPs are made from a multiferroic material that has the ability to couple magnetic and electric fields at room temperature. In contrast to electric fields, which are surface-limited and typically generated by invasive contact electrodes, magnetic fields generated by MENPs can penetrate the entire brain non-invasively and be controlled using external low-energy magnetic field. MENPs can be formed of material including iron, cobalt, zinc, cadmium, nickel, gadolinium, chromium, copper, manganese, terbium, europium, gold, silver, platinum, oxides of any of the preceding, alloys of any of the preceding, or mixtures thereof. Specific examples of MENPs include, but are not limited to, iron oxide, superparamagnetic iron oxide, $Fe_3O_4$, $Fe_2O_4$, $Fe_xPt_y$, $Co_xPt_y$, $MnFe_xO_y$, $CoFe_xO_y$, $NiFe_xO_y$, $CuFe_xO_y$, $ZnFe_xO_y$, and $CdFe_xO_y$, wherein x and y vary depending on the method of synthesis. A specifically contemplated material for producing MENPs is $CoFe_2O_4$—$BaTiO_3$.

MENPs facilitate efficient coupling between magnetic and electric fields at nanoscale (or microscale) over the entire brain volume. Once MENPs are present in the brain, remotely controlled magnetic fields (as opposed to electric fields) can be used to induce strong local electric charge oscillations in the MENPs that interact with the neural network. The interaction between the MENPs and the neural network can be used to induce localized and targeted drug release. The magnetic fields generated by the MENPs effectively and non-invasively penetrate the entire brain. The magnetic fields generated by the MENPs can be activated and deactivated remotely using external low-energy magnetic field sources such as external electromagnetic coils.

The MENPs must be manufactured with certain properties for the MENPs to be effective for use targeted delivery of therapeutic cargo. For example, the MENPs are small enough to penetrate the blood-brain barrier. In certain embodiments, the MENPs are smaller than: about 50 nm, than 40 nm, about 35 nm, about 30 nm, about 25 nm, about 20 nm, about 15 nm, or about 10 nm. In certain embodiments, the MENPs have sizes in a range of about 15-20 nm, in a range of about 10-20 nm, in a range of about 15-25 nm, in a range of about 10-50 nm, in a range of about 20-50 nm, in a range of about 20-40 nm, or in a range of about 10-30 nm. As such, MENPs are small enough to penetrate the blood-brain barrier and are able to move into selected brain regions to deliver therapeutic cargo to specific brain regions.

In certain embodiments, MENPs bound to the therapeutic cargo are encapsulated within liposomes, which results in the formation of therapeutic cargo-loaded magnetic liposomes. In certain embodiments, the liposomes provide biocompatibility for MENPs, allowing the therapeutic agent to pass the BBB by application of an external magnetic field. The therapeutic cargo-loaded magnetic liposomes can be further surface modified with specific affinity ligands, such as polyclonal/monoclonal antibodies, peptides, peptidomimetics, specific physiological ligands/analogues that target the MENPs containing liposomes to the brain.

The liposomes can be formed by known means, such as by mixture of phosphatidyl choline, phosphatidyl ethanolamine, and cholesterol. The liposomes optionally can further be formed with dihexadecyl phosphate (DHDP) and distearoyl phosphatidyl ethanolamine (DSPE). The liposomes further can include polyethylene glycol moieties. For example, the liposomes can be prepared using a phosphatidyl moiety further having a polyethylene glycol (PEG) moiety. The PEG moiety, if present, extends from the surface of the liposome into the surrounding environment. The presence of a PEG moiety stabilizes the circulating half-life of the liposomes and can further provide a sustained release type formulation for the therapeutic agents bound to the magnetic nanoparticles in the liposomes.

In one embodiment, MENPs have a coating over the magnetic material. Suitable coatings include dextran, chitosan, poly(lactic-co-glycolic acid) (PLGA), dendrimers, amphiphilic polymers/bio-polymers (e.g. phospholipids and peptides), surfactants or chemical compounds with chelating properties for magnetic nanoparticles or high affinity adsorption (e.g. both chemisorption or physical adsorption) on the surface of magnetic nanoparticles, silicon oxide, silica, silica-PEG, mesoporous structures (silica or polymers or their combinations), or any other preferred combination of the above. In some cases, the coating is an amphiphilic polymer, for example, a phospholipid-PEG coating.

In another embodiment, MENPs have a hydroxyl functional group on their surface, which allows for ionic binding of a therapeutic cargo to the surface of the MENPs. This binding can be reversible and allows for the bound drugs to be released at a target site. The amount of therapeutic agent bound to MENPs can be controlled by the molar ratio of therapeutic agent to MENPs, incubation time for mixing of the two components, the pH of the incubation, the temperature of the incubation, and/or the buffers used during the incubation. For example, phosphates interact strongly with iron oxide particles, and therefore, the presence of phosphates during incubation would impact the amount of therapeutic agent bound to the MENP surface.

The therapeutic agents can be bound to the surface of the MENPs through a variety of means, including ionic interactions and covalent bonds. Ionic interactions between therapeutic agents and MENPs can occur between charged moieties or moieties capable of hydrogen bonding on the therapeutic agent and the MENPs. Covalent bonds between the therapeutic agent and the MENPs are preferably hydrolysable or releasable, such as ester bonds. For MENPs having hydroxyl groups on the surface, an ester bond can be formed between a therapeutic agent having a carboxylic acid moiety and the MENPs.

The subject invention provides pharmaceutical compositions comprising a therapeutically effective amount of MENPs and, optionally, one or more pharmaceutically acceptable carriers. Such pharmaceutical carriers can be liquids, such as water. The therapeutic composition can also comprise excipients, adjuvants, flavoring agents, etc. that facilitate processing of the active compounds into preparations that can be used pharmaceutically. Proper formulation is dependent upon the route of administration chosen. In one embodiment, the pharmaceutical composition and all ingredients contained therein are sterile.

The term "carrier" refers to a diluent, adjuvant, excipient, or vehicle with which the compound is administered. Examples of suitable pharmaceutical carriers are described in "Remington's Pharmaceutical Sciences" by E. W. Martin. Such compositions contain a therapeutically effective amount of the MENPs formulation, together with a suitable amount of carrier so as to provide the form for proper administration to the patient.

In one embodiment, the administration of the composition can be systemic. Oral, intravenous, intra-arterial, subcutaneous, intra-peritoneal, intra-thecal, intra-muscular, intra-ventricular, intra-nasal, transmucosal, subcutaneous, topical, rectal, and other modes of administration are all contemplated. The compositions can be designed to facilitate the subject compositions to crossing BBB.

In one embodiment, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. Formulations can also be prepared for use in inhalation therapy. For administration by inhalation, the composition can be delivered in the form of an aerosol spray presentation from pressurized packs or a nebulizer, with the use of a suitable propellant. The composition can also be administered via inhalation or other route as a powder.

In particular embodiments, the therapeutic composition is a sustained-release system. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., Biopolymers 22:547-556, 1983, poly(2-hydroxyethyl methacrylate)); (Langer et al., J. Biomed. Mater. Res. 15:167-277, 1981; Langer, Chem. Tech. 12:98-105, 1982, ethylene vinyl acetate (Langer et al., Id.) or poly-D-(−)-3-hydroxybutyric acid (EP 133,988).

In one embodiment, implantable drug infusion devices may be used to provide patients with a constant and long-term dose or infusion of a therapeutic composition. Such device can be categorized as either active or passive.

In one embodiment, polymers can be used for ion-controlled release. Various degradable and non-degradable polymeric matrices for use in controlled drug delivery are known in the art (Langer, Accounts Chem. Res. 26:537, 1993). For example, the block copolymer, poloxamer 407, hydroxyapatite, and liposomes.

The pharmaceutical composition of the present invention may be used either alone or in combination with one or more drugs for treating HAND. The compositions can also be formulated in combination with at least one other agent, such as stabilizing or buffer compounds, which can be administered in any sterile, biocompatible pharmaceutical carrier, including, but not limited to, saline, buffered saline, dextrose, and water. In addition to MENPs and the therapeutic cargo, the compositions can contain suitable pharmaceutically acceptable carriers comprising excipients and auxiliaries that facilitate processing of the active compounds into preparations that can be used pharmaceutically. The composition may be prepared as a single-dose form using a pharmaceutically acceptable carrier or excipient or may be contained in a multiple-dose container.

The compositions described herein can be used to deliver drugs to a subject in a controlled release fashion by administering to the subject the MENPs conjugated to a therapeutic cargo. In an embodiment, MENPs form ionic bonds with therapeutic cargo and applying a magnetic field to the MENPs weaken the ionic bonds and release the cargo.

In one embodiment, MENPs in the formulations described herein contain (i) a coating on at least a portion of the MENPs surface, said coating one or more of glycerol monooleate, poly L-lysine and polyethylene glycol, and (ii) a therapeutic cargo conjugated with the MENPs through an ionic bond.

In certain embodiments, the MENPs comprise $CoFe_2O_4$—$BaTiO_3$. The MENPs can have a diameter of about 3 nm to about 100 nm, or about 5 nm to about 50 nm, or about 50 nm. The MENP can further comprise a coating layer. The coating layer can be, for example, one or more of glycerol monooleate (GMO), polyethylene glycol, and poly-L-lysine. In certain embodiments, the coating layer comprises GMO.

In certain embodiments, a composition described herein is administered to a subject and the active ingredients are guided by magnetic force across the BBB into brain parenchyma and released on demand by alternating current. Because of the three different active ingredients present in the claimed invention, namely, an HIV inhibitor, a BACE-1 inhibitor, and a cocaine antagonist, the compositions of the invention can reduce HIV infection, prevent or arrest amyloidogenesis, and/or cure neurocognitive deficits associated with HIV infection and cocaine addiction.

Accordingly, an embodiment of the invention provides a method of treating HIV infection in a subject, particularly, a subject having an HIV infection and cocaine addiction. "Cocaine addiction" as used herein, refers to a chronic, relapsing psychological condition characterized by compulsive cocaine seeking and use, despite harmful consequences.

The method comprises administering to the subject a formulation comprising MENPs conjugated to a therapeutic cargo comprising an HIV inhibitor, a BACE-1 inhibitor, and a cocaine antagonist. The method further comprises applying an alternating current magnetic field to the subject to induce local electric charge oscillations in the MENPs to induce release of the therapeutic cargo.

The description of various aspects of MENPs and therapeutic cargo discussed above in connection with the formulations of the invention are also applicable to the methods of treating HIV described herein.

In one embodiment, the invention provides a method of treating HIV infection in a subject, particularly, a subject having HIV infection and cocaine addiction, the method comprising administering to the subject a formulation comprising MENPs conjugated to or mixed with a therapeutic cargo comprising WA, miR-107, and a BD1063, the method further comprises applying an alternating current magnetic field to the subject to induce local electric charge oscillations in the MENPs to induce release of the therapeutic cargo.

Therapeutic efficacy of the combination of WA, miR-107 and BD1063 on HIV and cocaine-induced neuropathological hallmarks of HAND can be studied by using AβPP-transfected cells in culture. The therapeutic efficacy of the formulations containing MENPs conjugated with the active agents in the compositions described herein can be tested in cocaine-treated APP/PS1 Tat-injected mice as an in vivo model for HAND. Delivery of WA along with miR-107 and BD1063 leads the inhibition of HIV infection, the suppression of Aβ-deposition and improved neuro-cognitive functions in HIV-infected cocaine addicts.

Applying an AC magnetic field that equivalently sweeps all bond orientations can create a more uniform bond-breaking process over the surface of the MENPs and thus enhance the drug release efficacy. This can be achieved by using a spatially rotating field where the field profile is changing in time as well as in space. The field rotation in space can be accomplished, for example, by using an array of coils that generate alternating current fields with non-zero phase shifts with respect to each other, as illustrated in FIG. 2c of US20150283368. Certain aspects of the step of administering alternating current to the subject to cause the release of therapeutic cargo are described in US20150283368, for example, in paragraphs [0040] to [0056].

As used herein, the singular forms "a," "an" and "the" are intended to include the plural forms as well, unless the context clearly indicates otherwise. Further, to the extent that the terms "including," "includes," "having," "has,"

"with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of," "consisting," and "consists."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc.

"Treatment" or "treating" and grammatical variants of these Willis, as used herein refer to an approach for obtaining beneficial or desired results including but not limited to therapeutic benefit. A therapeutic benefit is achieved with the eradication or amelioration of one or more of the physiological symptoms associated with HAND such that an improvement is observed in the patient, notwithstanding that the patient may still be afflicted with HAND.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Preparation and Characterization of MENPS

Figure 1B:
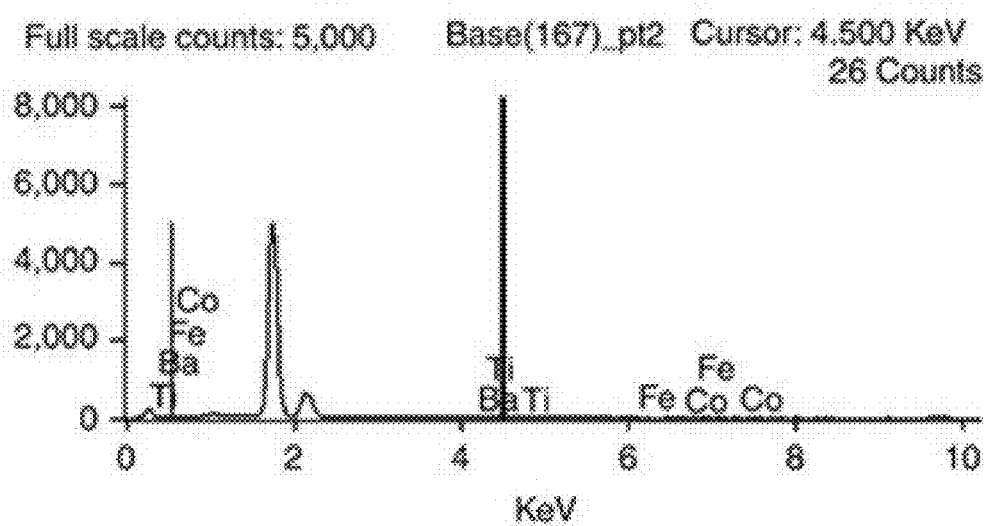

MENPs utilized as nanocarriers for BBB delivery were synthesized. Particle size, shape, charge distribution, phase purity, crystallinity, functionality, and magnetism of MENPs were studied using transmission electron microscope (TEM), X-ray diffraction (XRD), Zeta-sizer, Raman, and Vibrating sample magnetometer (VSM). TEM studies indicated that ferromagnetic MENPs are of ~20±3 nm in size (FIG. 1a), no agglomeration and exhibited all atomic planes of both precursors, i.e., CFO ($CoFe_2O_4$) and BTO ($BaTiO_3$), were perfectly crystalline and showed all functional groups of CFO and BTO (FIG. 1b).

Example 2—Binding of MIR-107 and its Release from MENPs

Figure 2A:
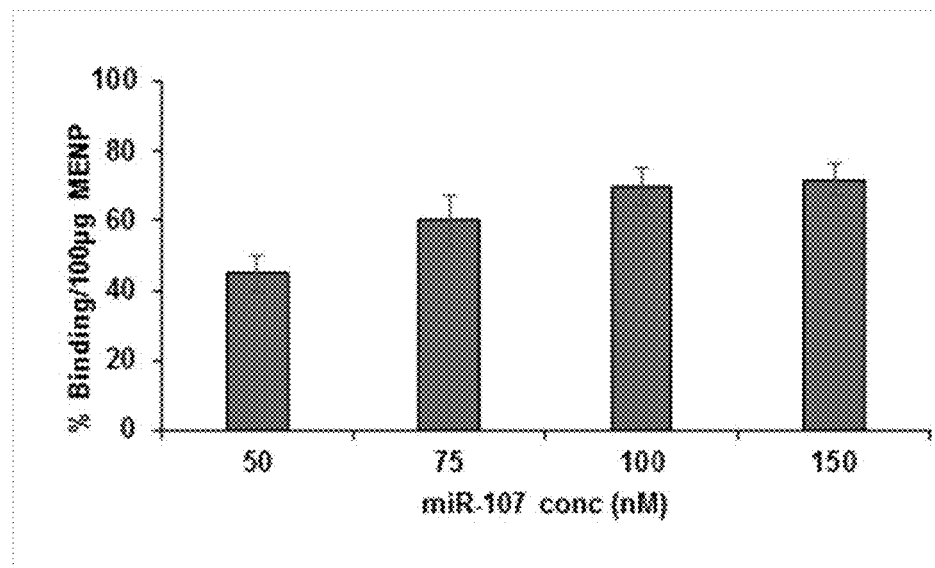
FIGS. 2A-2B provide miR-107 binding and release. A) % binding of miR-107 with MENP with respect to different concentrations; B) Release kinetics of miR-107 from MENP surface as a function of externally applied alternating current magnetic field strength (60 and 80 Oe) at different time points (10, 20 and 30 min).
Figure 2B:
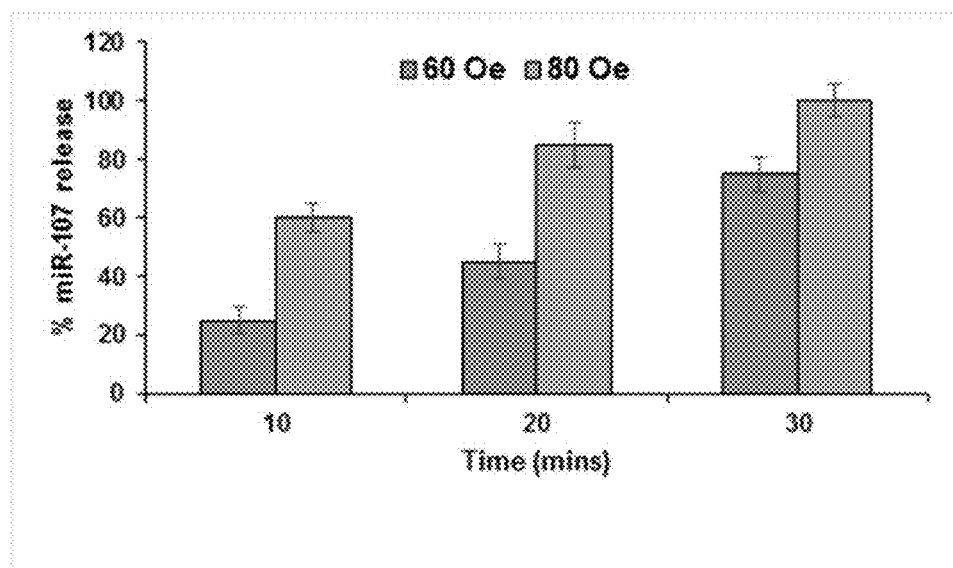

Binding kinetics with respect to different concentrations of miR-107 was performed using 100 μg of MENPs (FIG. 2A). Sample were incubated in phosphate buffered saline (PBS) (pH-7.4) and kept on vertical rotator under constant rotation (200 rpm) for 30 minutes. Results showed a concentration dependent increase in binding profile and maximum of 70% miR-107 binding was achieved at 100 nM. Release kinetics of miR-107 from MENPs was studied using UV spectroscopy at 260 nm. 100 nM of miR-107 was incubated with 100 μg of MENPs in 1 mL PBS (pH 7.4) for 30 mins and its release kinetics performed using alternating current magnetic field via electromagnetic coil at various time points (i.e., 10, 20, and 30 minutes). Result showed that alternating current stimulation causes polarization in MENPs and almost 100% release of miR-107 was accomplished using 100 Hz frequency at 80 Oe magnetic field compared to 75% at 60 Oe in 30 mins (FIG. 2B).

Example 3—WA and MENPS Did not Affect BBB Integrity

Figure 3A:
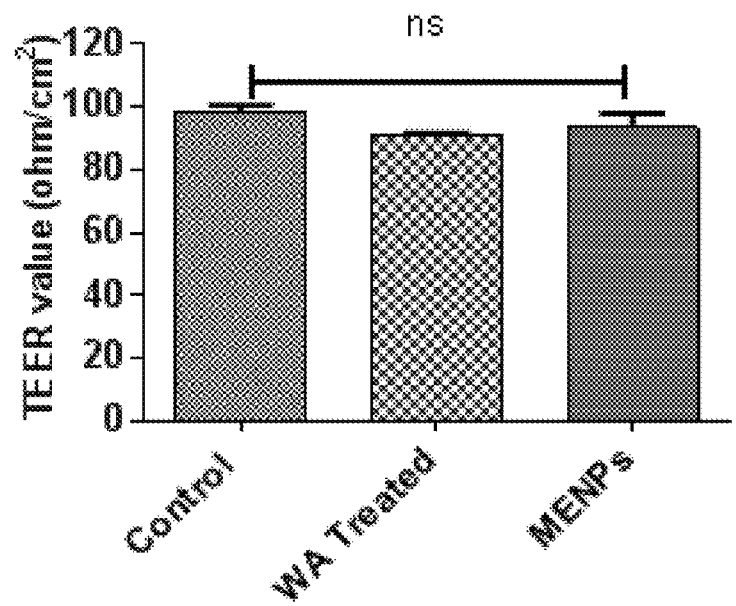
FIGS. 3A-3B provide: A) Effect of WA and MENP on in-vitro BBB integrity: WA (2 µM) and MENPs (100 µg) were added in the upper chamber of the BBB model with magnet (0.8 T) placed underneath the culture plate for 3 h duration. After treatment, Transepithelial Electrical Resistance (TEER) values were calculated and compared with control; B) Aβ1-40 ELISA from supernatant from SHAPP cells: To study WA (2 µM) efficacy and BBB permeability without MENPs, Aβ1-40 specific enzyme-linked immunosorbent assay (ELISA) was performed using supernatant collected from the basal side of the BBB trans-well where SHAPP cells were seeded at the bottom of culture plate. (n=3; NS-Not Significant.)
Figure 3B:
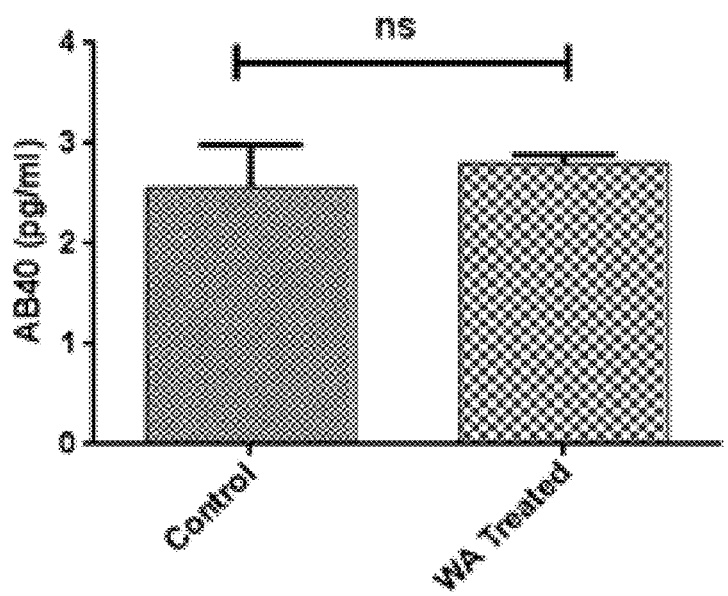

In-vitro BBB model was developed using brain microvascular endothelial cells, astrocytes and pericytes. The integrity of BBB was examined by measuring the TEER values before and after addition of free WA (2 μM) and free MENPs (100 μg) to the apical chamber of in vitro BBB model. There was no difference in TEER values when compared with MENPs or WA treatment alone (FIG. 3a) under the influence of external magnetic field (0.8 T). Free WA could not cross the BBB without being bound to MENP and therefore, no changes in the Aβ-secretion in SH-APP cells were observed (WA without MENP in the apical chamber) in comparison to the untreated control cells grown in the basal chamber of the BBB model (FIG. 3b).

Example 4—In Vivo BBB Transport and Cytotoxicity of MENPS

Figure 4A:
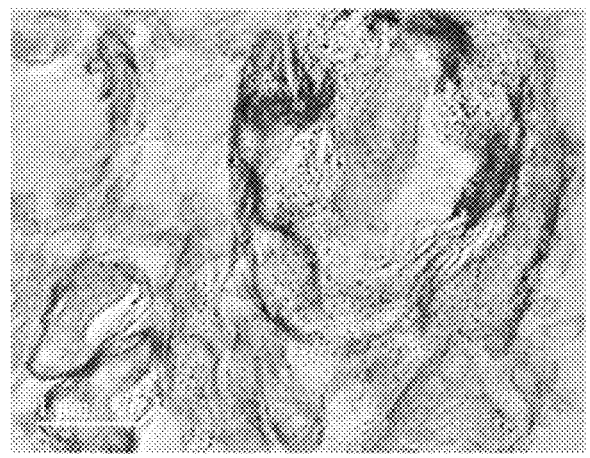
FIGS. 4A-4D provide: Validation of MENP's presence in the brain tissue after magnetic treatment. A & B: Ex-vivo TEM image of MENPs injected mice (10 mg/kg dose) arrows and circle shows the presence of MENPs in the tissue; C & D: STEM study was performed to study elemental composition using EDS and diffraction pattern for the evaluation of MENPs crystallinity and purity in the brain tissue sample after magnetic treatment.
Figure 4B:
Figure 4C:
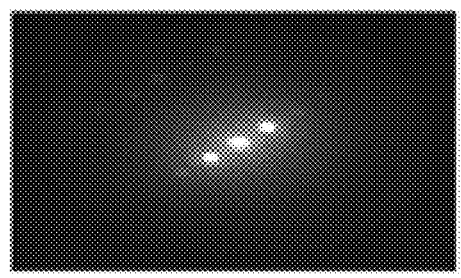
Figure 4D:
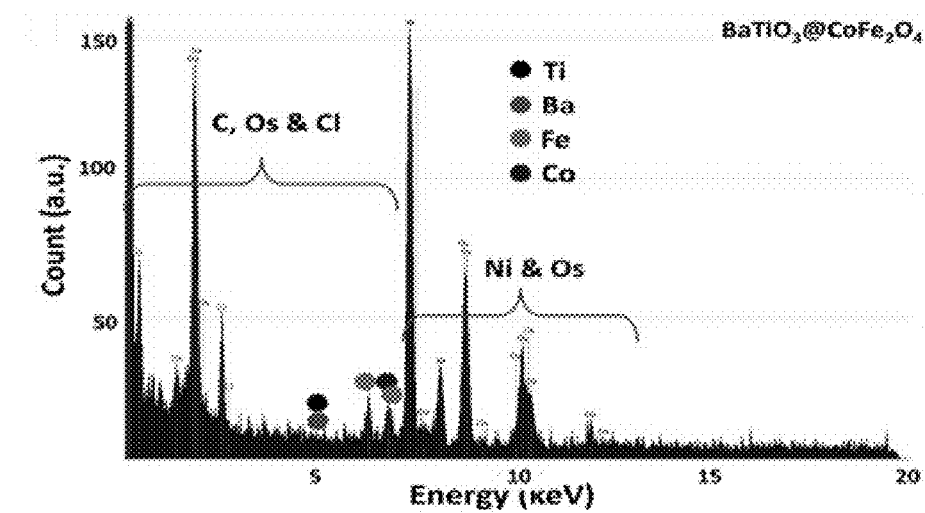

In-vivo TEM imaging of brain tissue and cytotoxicity evaluation of MENPs are given in FIG. 4. TEM imaging was used to evaluate MENP's (size: 20 nm, dose: 10 mg/kg) transport across BBB under the influence of external magnetic treatment (0.8 T for 3 h) and its distribution in the C57B1/J mouse brain using PBS injected as control under identical experimental conditions. After magnetic treatment, animals were scarified and brain sample were collected following perfusion. Whole brain was cut into two hemispheres and further cut into 8 transverse blocks. The blocks were processed and analyzed for qualitative and quantitative uptake of MENPs using in situ TEM analysis. MENPs (FIGS. 4a & b) were uniformly distributed (no agglomeration) across all the brain sections compared to control brains. To evaluate chemical composition of injected MENPs, high resolution transmission electron microscope (HRTEM) was employed to study the energy dispersive spectroscopy (EDS) and convergent beam electron diffraction (CBED)

patterns (FIGS. 4c & d). The EDS pattern showed the presence of all elements present in MENPs and CBED also exhibited the diffraction pattern of MENPs, thus, confirming that MENPs do not compromise its chemical composition and crystallinity after reaching the brain under the influence of noninvasive external magnetic field. An in vivo cytotoxicity evaluation was also performed for MENPs at different doses (10, 15, 20, 30 mg/kg) using histopathology (hematoxylin and eosin staining) of brain, liver, kidney, and spleen. H&E staining showed no recruitment of macrophages or other immune cells at any brain location. For acute peripheral toxicity (blood toxicity: 48 h) of the MENPs, the CBC analysis, biochemistry panel, and enzyme function tests were performed. Hematological parameters indicated no significant changes in comparison to the untreated control group and no difference was observed for hepatic and renal function tests and enzyme levels, when compared with the control group.

Example 5—Novel Magnetic Nanoparticles and Methods of Using Them

Magneto electric liposomes comprising MENPs conjugated to or mixed with WA, miR-107, and BD1063 was tested using HIV infected in vitro BBB model and cocaine treated transactivator of transcription (Tat) injected APP HAND mouse models. MENPs formulations can be used to deliver the therapeutic cargo to the target site guided by the external magnetic force by releasing the drugs in response to alternating current in a non-invasive manner in HIV infected APP transfected cell culture model, in vitro BBB model, and cocaine treated Tat-injected APP HAND mouse model. Successful delivery of WA, miR-107, and BD1063 would inhibit HIV infection, suppress Aβ-deposition and/or prevent hyper tau phosphorylation that would improve neurocognitive functions in HIV infected cocaine addicts.

MENPs have been designed to have adequately high magnetic moments and therefore, can be used for targeted delivery to desired body areas (including brain) by applying remote alternating current magnetic fields. This novel on-demand drug delivery technique based on the MENPs can serve as a pharmacological cargo carrier for targeted delivery against HIV infection. miR-107 can be directly immobilized on the surface of MENPs via electrostatic interactions between surface charges on MENPs and miR molecules. BD 1063 can be encapsulated in the hydrophilic core and WA can be encapsulated within the hydrophobic part of the liposomes via an extrusion method along with MENP-miR-107 assembly. Thus, the MENPs formulation provides a rationalized system to reduce HIV infection, β-secretase levels and activity, Aβ deposition in the brain and prevent the deleterious effect of cocaine abuse, such as Tau hyperphosphorylation.

Figure 5A:
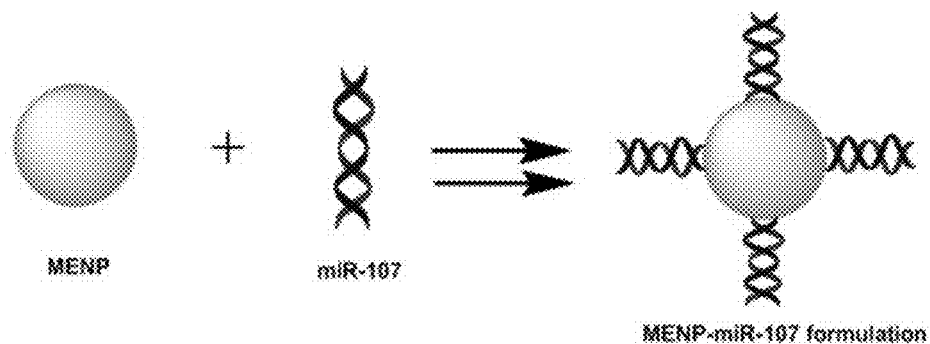
FIGS. 5A-5C provide illustration of magneto-electric liposome formulations for the delivery of miR-107, WA and BD1063 across the BBB: A) Binding of miR-107 to MENP based on electrostatic interaction; B) Encapsulation of WA (hydrophobic part) and BD1063 and MENP bound miR-107 (hydrophilic part) of liposome matrix; C) BD1063 and WA would be released from liposome either via biodegradation or diffusion. miR-107 would be released on-demand using alternating current trigger stimulation.
Figure 5B:
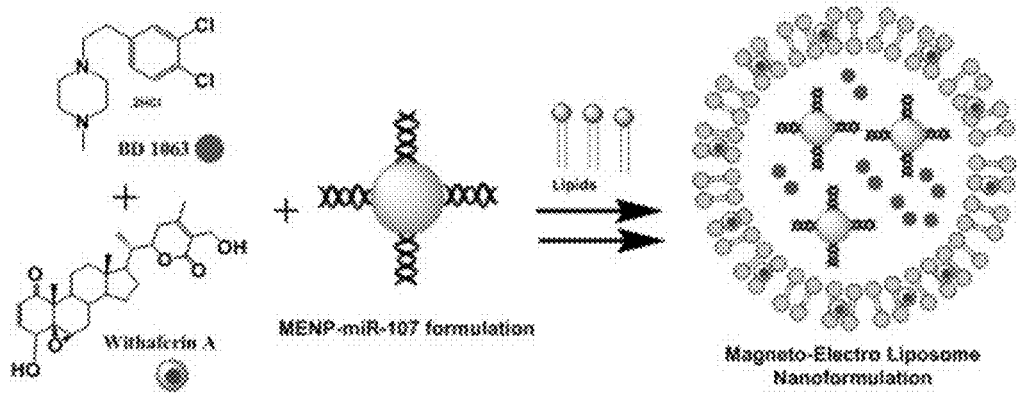
Figure 5C:
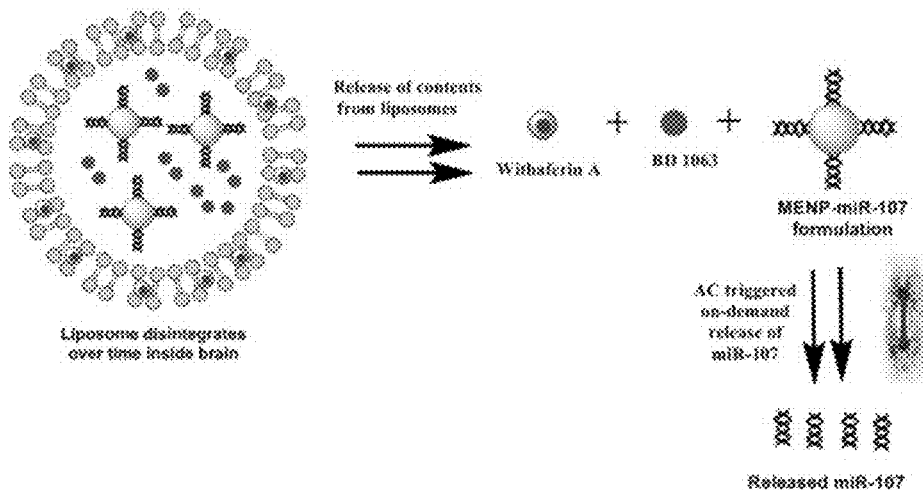

A schematic overview of the formulation design and its release mechanism is explained in FIG. 5.

Example 6—Therapeutic Efficacy of WA, MIR-107 and BD1063 on HIV and Cocaine Induced Neuro-pathological Hallmarks of Hand Efficacy of WA on inhibition of HIV infection in AβPP cell culture models: SH-SY5 (AβPP transfected cells) can be treated with various concentrations of WA before/after exposure to HIV (HIV-1 clade B (X4): NIH AIDS Research & Reference Reagent Program Cat #398). Cells can be exposed to a concentration of 103.0 tissue culture infected dose (TCID) 50/ml cells for up to 7 days. Cell culture supernatant can be collected and HIV infectivity levels can be measured using the p24 ELISA (Cat #0801200, ZeptoMetrix Corp). Further, the mechanistic role of WA on HIV inhibition can be studied at different levels, for example: a) viral entry: by episomal and integrated proviral DNA by qRT-PCR, b) transcription: using chronically infected cell line HUT78/HIV-1$_{SF2}$ (aids reagent #279) by qRT-PCR for HIV mRNA, c) Tat: by sandwich ELISA or western blot, d) Negative regulatory factor (Nef) protein: by western blot and e) NF-kb: using HEK293 transfected with pNL-Luc (aidsreagent.org #3418).

Efficacy of WA on Aβ1-40 and 1-42 accumulation can be tested in AβPP cell culture models exposed to HIV and cocaine. Transfected cells can be exposed to HIV-1± cocaine and treated with different doses of WA. Optimal concentration of cocaine can be determined. For example, doses from 0.1, 0.25, 0.5 and 1 µM can be used in AβPPP cell culture. Since, non-amyloidogenic processing of AβPP occurs at plasma membrane and amyloidogenic processing of AβPP happens only when AβPP is internalized into endolysosomes, western blot and immunostaining analysis can be used to determine AβPP levels and distribution (total, plasma membrane, and endolysosome) using an anti-AβPP antibody (Abcam, Cat # ab32136). Also, to determine the effects of WA on levels and distribution (total, plasma membrane, and endolysosome) of α-secretase, β-secretase (Anti-BACE1 antibody, Abcam # ab2077) and γ-secretase (Anti-Presenilin 1 antibody, Abcam Cat # ab71181), western blot and immunostaining analyses can be performed. Alternatively, SH-SY5Y AβPP-transfected cells can be treated similarly to determine the effects of WA on activity of α-secretase (α-secretase Activity Assay Kit, AnaSpec, Cat # AS-72085), β-secretase (BACE Activity Assay Kit, Millipore Cat #565785-1KIT) and γ-secretase (APH1A ELISA Kit, Aviva Systems Biology, Catalog # OKEH00431). Because both β-secretase and γ-secretase are located in endolysosomes and their activities are pH dependent, endolysosome pH can be measured ratiometrically using a lysoSensor dye (LysoSensor Yellow/Blue DND-160, Invitrogen). Finally, secretion of Aβ 1-40 and 1-42 in the culture supernatant as well as intracellular accumulation of Aβ 1-40 and 1-42 in cell lysates can be determined by using ELISA (Cat #KHB3481-β40, KHB3441-β42, Life technologies, USA).

Efficacy of miR-107 on β-secretase levels and activity can be tested in cultured cells exposed with HIV±Cocaine. Aβ producing cells can be treated with HIV-1 and/or cocaine followed by transient transfection with optimum concentrations of miR-107 as determined experimentally using various doses. Scrambled miRNA can be used as a control. The protein levels and activity of BACE-1 can be determined.

Effect of cocaine can be studied on HIV infection, Tau-phosphorylation and Aβ levels and its reversal using BD1063. SH-SY5Y AβPP-transfected cells can be exposed for 2 h with an optimized ratio of BD1063 (ratio of BD1063 to Cocaine: 1:1, 1:2, 1:4) before addition of cocaine and incubated for a preset time. Cells can be harvested at different intervals (ranging from 6, 12, 24 and 48 h) to determine the effects on Tau-phosphorylation and Aβ deposition. In another set of experiments, SH-SY5Y AβPP-transfected cells can be exposed to HIV-1 and cocaine in combination with BD1063 (at different ratio to cocaine i.e. 1:1. 1:2, 1:4) as described above and can be incubated for 7 days. After 7 days of infection, HIV infection levels can be measured by using the p24 ELISA; and Tau-phosphorylation and Aβ deposition was measured as described above.

Efficacy of WA, miR-107 and BD 1063 on AβPP cell culture model can be tested. A combinatorial therapeutic approach comprising WA, miR-107 and BD1063 can be tested in SH-SY5Y AβPPP-transfected cells exposed to HIV-1±cocaine (7 days). These cells can be transfected with miR-107 and simultaneously treated with WA and BD1063 at optimized doses and incubation times. Cells can be analyzed for HIV-1 infection (p24 ELISA), mature and immature AβPPP levels, α, β, γ-secretase levels and activities, Tau-phosphorylation and Aβ1-40 and Aβ1-42 deposition can be determined as described above.

Example 7—To Develop, Characterize Magneto-electric Liposomal Nanoformulation (NF) of WA, MIR107 & Cocaine Antagonist MENPs formulations of WA, miR107, and BD1063 can be characterized and studied using non-invasive BBB transmigration, and controlled release of the therapeutic cargo using in vitro BBB model.

Preparation of $CoFe_2O_4$—$BaTiO_3$ core-shell nanoparticles (MENPs): MENPs can be prepared according to the hydrothermal method. The particle size of synthesized $CoFe_2O_4$—$BaTiO_3$ nanoparticles can be estimated using transmission electron microscopy (TEM), Zeta-sizer and x-ray powder diffraction (XRD) characterization of nanoparticle can be done to determine the crystalline properties of the MENPs. The nanoparticle size would be about 20-30 nm.

Binding of miR-107 on MENPs: The surface charged MENPs would bind to the miR-107 via electrostatic interactions (MENP-miR-107). The binding procedure can be standardized by using different concentrations of MENP to miR-107 as described. Further, the miR-107 bound MENPs can be characterized by TEM for size, shape, charge and presence of miR-107 on MENPs. Optimized amount of miR-107/μg MENP can be used for liposomal formulation.

Preparation, characterization of PEGylated magneto-electric liposomes (MELs) and encapsulation efficiency evaluation: PEG-MELs can be synthesized using an extrusion method. Similar methodology can be adopted for the development of liposomal MENPs formulations using optimized 7:2:0.5 molar ratios of Egg Phosphocholine (PC), Cholesterol (CL), and mPEG2000-DSPE. Hydrophilic lipid core would encapsulate PBS dissolved MENPs+miR-107 and BD1063 component and hydrophobic lipid part would encapsulate WA. Unencapsulated MENPs, drugs and siRNA can be removed by centrifugation at 15,000 rpm for 30 minutes. Finally, formulations can be characterized for MENPs size (TEM, Zeta-sizer), shape (TEM), charge (Zeta-sizer) and % loading efficiency of individual molecules (miR-107, WA and BD1063) using high-performance liquid chromatography (HPLC). Different concentration of MENPs+miR-107 can be optimized to achieve maximum anti-miR107 loading and its BBB transmigration under the consideration of overall size of MENPs (120±10 nm).

Stability evaluation of the MENP formulations: The magneto-electric liposomal formulations can be checked for stability using an in vitro closed circulatory peristaltic pump system (Fisher Scientific). MENPs+miR-107 and WA+BD1063 physicochemical interactions within the liposomes can be studied using differential scanning calorimetry (DSC) and Fourier-transform infrared (FTIR). Also, localization of WA, BD1063 and MENPs in the lipid membrane of the liposomes can be done using $^{13}C$ and $^{31}P$ solid state nuclear magnetic resonance (NMR). Further, the MENP formulations can be studied for long term stability at 5° C.±3° C. (for 6-12 months) and accelerated stability at 25° C.+2° C./60%±5 relative humidity (RH) (for 3-6 months) using thermal stability analysis. This aspect of liposomal MENPs formulations described herein would achieve better drug pharmacology with minimum or no drug-drug interaction within the formulations.

In-vitro drug release kinetics of NFs: In-vitro drug release can be studied in PBS (pH-7.4) and simulated cerebrospinal fluid (CSF) using a closed circulation peristaltic pump system at 37° C. and analyzing released miR-107/WA/BD 1063 using high performance liquid chromatography mass spectroscopy (HPLC/MS). The peristaltic pump system (bi-directional, self-priming peristaltic capillary pump) would simulate real in vivo physiological blood-circulation and facilitate stability analysis. Also, to optimize the miR-107 release from MENPs, external magnetic field at different field strengths (12, 44, 66 & 800e) and frequencies (0, 100, 1,000 Hz) for different treatment durations (1, 5, 10, 60 and 120 min) can be applied to optimize release kinetics.

Preparation and validation of BBB integrity: Established in vitro BBB model can be used. The BBB model can be constructed using primary endothelial cells (HBMEC), pericytes (HMVP) and astrocytes (HA). BBB formation and intactness can be determined by measuring the TEER using the REMS AutoSampler BBB device and permeability to fluorescein isothiocyanate-dextran (FITC dextran). A mean TEER value of 100 and over $\Omega/cm^2$ cell culture insert would be consistent with the formation of a functional BBB. The in-vitro BBB model can be validated by measuring the expression of tight junction proteins ZO, claudins, occluding, and Junctional adhesion molecule (JAM) by immunostaining and real time polymerase chain reaction (PCR). All the cells used for in vitro BBB formation are part of human system and would mimic the in vivo scenario.

Transmigration of magneto-electro liposomal MENPs formulations across in vitro BBB model: All transmigration assays can be conducted on day 5 of BBB culture once the membrane integrity has been established by TEER measurement. The nanoparticles formulations can be added to the apical chamber of in vitro BBB culture and its transport across the BBB can be monitored after application of an external magnetic field using different external magnetic fields (0.3-0.8 Tesla) and transmigration can be optimized at different time points. The miR-107, WA, BD1063, MENPs and MENPs+miR-107 can be used as a control and used to evaluate the overall MENPs transmigration. Maximum MENPs would cross the BBB on application of optimized non-invasive external magnetic field and would not show any side effects to CNS cells.

MENP efficacy evaluation in AβPPP cell culture model: SH-SY5Y AβPP-transfected cells can be cultured with HIV± cocaine in the basolateral chamber of the BBB model. Liposomal MENPs can be added apically to the BBB inserts. On 7 days of post-exposure, cells can be analyzed for HIV infection (p24 levels), β-secretase levels and its activity, Aβ 1-40 & 1-42 deposition and Tau hyperphosphorylation. Therapeutic agents are frequently expelled from the CNS by efflux transporters that are expressed by brain endothelial cells. Therefore, the studies can be expanded to evaluate the impact of MENPs on the expression and activity levels of P-glycoprotein (P-gp), breast cancer resistance protein (BCRP), and multidrug resistance proteins (MRPs). Among the large family of MRPs, primarily focus would be on MRP1, which is upregulated by Tat protein.

MENPs cytotoxicity and cell uptake study: MENPs cytotoxicity can be determined in peripheral cells (PBMC) and different primary CNS cells (microglia, astrocytes and primary neurons) using MTT & XTT cell viability and cytotoxicity assay for at least up to 7 days of treatment. Confocal microscopy and flow cytometry can be done to estimate the qualitative and quantitative analysis for cell uptake for fluorescently tagged MENPs. Additionally, inflammatory cytokine and oxidative stress arrays can be performed to measure the functional effects of free miR-107/WA/BD1063 and liposomal NFs on the CNS cells. MENPS that would show no cytotoxicity to periphery and CNS cells and no reaction to blood components can be used for in vivo studies.

Example 8—Biological Efficacy, Controlled Release and Biocompatibility of Therapeutic Cargo in Cocaine Treated APP/PS1 TAT Injected Hand Mouse Model The APP/PS1 mouse model exhibits remarkable elevation of Aβ production associated with certain behavioral abnormalities. Also, injection of stereotaxic Tat into the hippocampus of APP/PS1 transgenic mice creates the HAND pathology in the brain and induces the Tat-mediated production and processing of Aβ in vivo. Because cocaine induces the Tau-hyper phosphorylation, APP/PS1 mice can be injected with cocaine with/without HIV-1 Tat protein to mimic the brain pathology of HIV infected patients with cocaine abusers. This can be designed to validate the outcome of the pre-screening studies using HAND mouse model and to evaluate the transmigration of the MENPs across the BBB under the influence of an external magnetic field. This was also designed to study the controlled release on alternating current stimulation and efficacy of the developed MENPs formulations in APP/PS1 mouse model for inhibiting Tat+ Aβ induced neurocognitive impairments in presence of cocaine.

Injection of HIV-1 Tat and Cocaine into the APP/PS1 mouse model: In APP/PS1 transgenic mouse model, maximum levels of Aβ deposition in the brain and behavioral changes have been reported at 6-8 months of age. Therefore, HIV-1 Tat protein can be injected stereotaxically into the hippocampus of the APP/PS1 mice of 8 months old. Cocaine hydrochloride (Sigma) can be dissolved in 0.9% physiological saline and 10 mg/kg of cocaine can be administered intra peritoneal (I.P.) into adult mice (25-30 g, n=10). Adult mice can be assigned into treatment groups receiving: (i) PBS injection and (ii) Tat injection. 25 μg/1 μL of Tat1-101 in PBS can be injected into the right hippocampus using small animal stereotaxic apparatus. Mice can be anesthetized with isoflurane and under aseptic conditions a midline scalp incisions can be made to expose the surface of the skull. Using bregma as a landmark, a burr hole can be made with a 26-gauge needle at the selected site and all injection volumes can be 1 μl using a 10-μl Hamilton syringe for a period of 1 min. The stereotaxic coordinates for this study can be centered on the dentate gyrus as follows: anteroposterior (AP)=−3.8 mm and mediolateral (ML)=+2.5 mm (from bregma) and dorsoventral (DV)=3.0 mm ventral to dura. Following Tat injection, the needle can be left in place for one minute before its withdrawal. The scalp can be cleaned with sterile saline and skin closed with sterile wound clips. Tat protein can be derived recombinantly (commercially available from ImmunoDX) and can be non-infectious, sterile, and endotoxin free. Tat protein would cause local inflammation and resultant histopathological changes can be determined by Hematoxylin and eosin staining and any pathological changes can be correlated by neurobehavioral studies (as described below).

Animal groups: The efficacy and neurobehavioral aspects of developed MENPs can be tested using different type of mouse model system i.e. 1) APP/PS-1; 2) APP/PS-1-treated with Tat; 3) APP/PS-1 treated with cocaine; and 4) APP/PS-1-HAND treated with Tat and cocaine. Mice can be categorized and treated with 5 different MENPs treatment, i.e. MENPs groups: 1) Control with PBS injected; 2) MENPs alone; 3) MENPs+miR107; 4) Liposome encapsulated MENPs+miR107; 5) Liposome loaded with WA+BD1063+MENPs+miR107.

Dosage evaluation of liposomal MENPs: 10 animals/group (5 Groups) can be used for the proposed in vivo efficacy studies. Doses of MENPs at 5, 10 and 20 mg/kg can be used to obtain the dose response curve for amyloid accumulation, BACE-1 protein and activity levels and Tau-phosphorylation. The optimum dose for formulation of the final MENPs would be selected. Five groups of mice can be selected for the time dependent study (3, 5 and 7 days, selected based on liposome release profile) including control (10 mice/group/treatment). After post-MENP treatment, animals can be sacrificed at predefined time for immunohistochemistry, neurotoxicity and reduction in Aβ levels.

Immunohistochemistry for Aβ deposition: Immunohistochemical data can be analyzed by using the standard protocol. Brains (prefrontal, parietal, and piriform cortices) can be excised and fixed in 4% paraformaldehyde, transverse sections (18/20 μm thick) can be cut on cryostat and mounted on Superfrost Plus (Menzel Glaser, Madison, Wis.) slides. Sections can be pretreated with $H_2O_2$, in phosphate-buffered saline at 37° C. for 15 minutes to eliminate endogenous peroxidase, and can be rinsed twice in 0.05 M Trizma buffered saline containing 0.1% Tween-20 at pH 7.4 (TBS-T) for 10 minutes each, pretreated with blocking Avidin/Biotin kit, and then incubated overnight at 40° C. with the primary antibodies to total Aβ (clone 6 F/3D, Dako), Aβ1-40 (Merck Millipore, Billerica, Mass.), Aβ1-42 (Merck Millipore). The sections can be washed with PBS and reacted with biotinylated secondary antibodies and visualized using ABC Elite kit (Vector Laboratories, Burlingame, Calif.). Sections can be lightly counterstained with hematoxylin. The total Aβ burden can be calculated as the percentage of the area of Aβ deposition in plaques with respect to the total area. The ratios between Aβ1-40 and Aβ1-42 deposition can be calculated by comparing specific staining with each antibody in consecutive sections. Beta-amyloid quantification can be assessed using the Adobe Photoshop CS4 software (Adobe Systems Inc., CA).

Analysis of Tau-phosphorylation: Part of the brain samples from all the treatment and control groups can be collected, sonicated and the total protein can be isolated, and the Tau-phosphorylation can be measured by using the western blot as described above.

Magnetic targeting and functional Magnetic Resonance Imaging (fMRI) for bio-distribution and navigation studies: For exposure of magneto-electric fields, animals can be anesthetized with a mixture of 1.5% isoflurane/air and the caudal vein was cannulated using a 26 gauge angiocatheter. The animals can be placed on a platform with their head positioned between the poles of an electromagnet. After adjustment of magneto-electric field, animals can be injected i.v. with MENPs through the caudal (tail) vein and retained in the field for 3 hrs. All the fMRI can be performed with a 12 cm horizontal bore, 4.7 Tesla Agilent Imaging systems. A single slice gradient echo sagittal image can be acquired to facilitate reproducible positioning of the animal head within the coil using the base of the skull as a reference. The time course of NF distribution can be monitored by serial acquisition of GE and T2 weighted magnetic resonance imaging (MRI) scans. Images can be acquired before and after administration of MENPs and after magnetic targeting for 30 min intervals over a 4 h period.

Neurobehavioral studies in MENPs treated HAND/Tat mouse model: Before the mice scarified for MENPs formulation efficacy evaluation, neurobehavioral studies can be performed using the same animals from each group. This would help reducing the animal numbers and overcome errors of cocaine and Tat treatment. Mice injected with MENPs can be tested for locomotor activity (LA) altered due to the cocaine administration and Tat injection. Batteries of neurobehavioral tests mentioned below can be performed to assess any neurobehavioral alternation due to MENP formulations, loaded therapeutic agents, or any chemical component.

Locomotor Sensitization: Locomotor activity can be measured in a circular corridor with four infrared beams placed at 90° angles (Imetronic, Pessac, France) in a low luminosity environment. Counts can be incremented by consecutive interruption of two adjacent beams (i.e. mice moving through ¼ of the circular corridor).

Rotarod Test: The motor strength, ability, balance, and coordination skills of all the experimental mice in all treatment and control groups can be evaluated in a rotarod apparatus (RotaRod-5; San Diego Instruments, San Diego, Calif., USA). Mice can be placed on the rod without any training period and the rod was accelerated from 1 to 40 rpm in 1.0 rpm steps per 15 s. The time the mice spent on the rod without falling can be recorded.

Fear Conditioning/Active Avoidance: This fear-motivated associative avoidance test is based on electric current where the mouse should learn to predict the occurrence of this aversive event by actively moving to a different compartment (escape platform). This active avoidance task provides a simple way to assess associative learning and memory by testing the ability of the mouse to avoid an aversive event in response to a stimulus cue.

A novel object recognition test: Long-term impairment of hippocampal-dependent cognitive functions can be assessed using the novel object recognition test as an indicator of short-term memory. This test is based on a natural tendency of rodents to spend more time interacting with new objects relative to familiar objects. On the day before the experiment, mice can be acclimated to an empty, clear plastic cage for one hour. The tested mice can then be put back into the same cage and allowed to freely explore the cage containing two identical objects. Four hours after this initial trial, the mice can be tested for memory using the same procedure, except that one of the familiar objects is replaced with a new object. The cumulative time spent exploring each object can be recorded. Exploration is defined as actively touching or facing (within 2 cm) the object. The time of exploration of each object [Tf and Tn for familiar (f) and novel (n) objects, respectively] can be recorded for determination of the recognition index (RI)=Tn/(Tf+Tn).

Morris Water Maze to Assess Spatial Learning and Memory: The spatial learning and memory ability of mice can be tested and analyzed using the Morris water maze. The training paradigm for the hidden platform version of the Morris water maze can be conducted in 4 trials (60 s maximum; interval 15 min) each day for five consecutive days. The probe trial can be carried 2 h after the completion of training on day 5. The visible platform task can be conducted in 4 trials each day for 2 consecutive days with the escape platform marked by a visible cue and moved randomly between four locations. The trajectories can be recorded with a video tracking system.

Example 9—WA Inhibits HIV Infection and HIV Induced Amyloid Beta Production

Figures 6A, 6B, 6C:
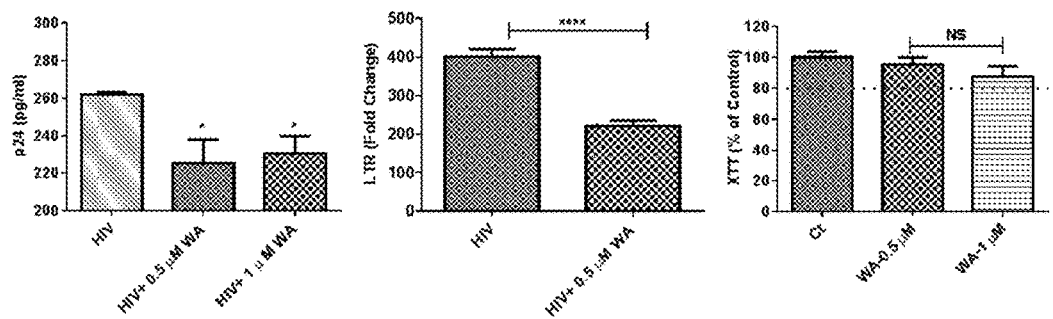
FIGS. 6A-6C show Effect of WA on HIV-1 suppression and its cytotoxicity in microglial (CHME-5) cell±HIV. A significance decrease was observed in the HIV infection levels in CHME-5 cells infected with HIV-1 on WA treatment. (A) p24 study; (B) LTR and (C) Cytotoxicity study: XTT assay was performed on WA treated CHME-5 cells (n=3; *, p≤0.05; ****, p≤0.001; NS-Not Significant).

Human microglial cells (CHME-5) were infected with HIV and treated with different concentrations of WA (0.5 and 1 µM). Seven days post-infection (dpi), culture supernatant was used for p24 ELISA and cell pellet was used for the long-term repeats (LTR) measurement using quantitative real-time PCR. A significant suppression of HIV-1 replication by both the tested concentrations as evident by decreased levels of p24 (FIG. 6A) and LTR levels (FIG. 6B) even at lower concentration of WA (0.5 µM). Also, cytotoxicity of the WA at 0.5 and 1 µM was measured by using the XTT assay and the results showed no cell death (>80% cell viability) of CHME-5 cells treated for 48 hours with 1 µM WA (FIG. 1C).

Figure 7A:
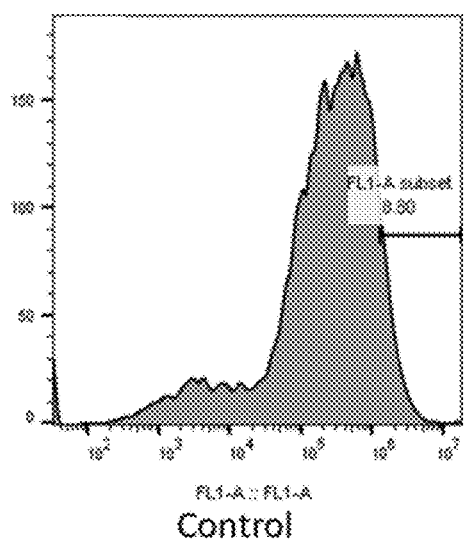
FIGS. 7A-7D show quantitative analysis of β-amyloid production after 7 days of HIV infection and 48 hours of WA treatment (2 µM) on SH-APP (neuroblastoma cell line) using flow cytometry. An increase in β-amyloid production is observed in cells treated with B) HIV-100 ng; compared to A) Control. HIV induced Aβ (B) was significantly decreased by WA(C) to similar control level (A); Overlap (D).
Figure 7B:
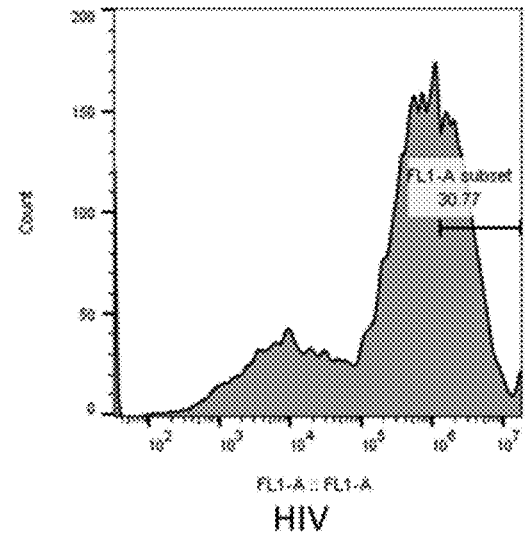
Figure 7C:
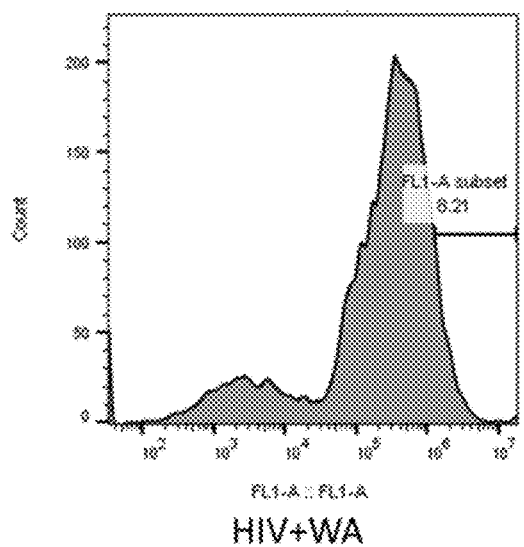
Figure 7D:
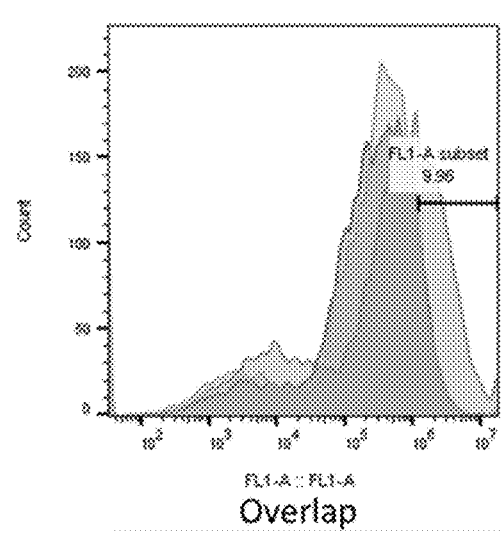

FIGS. 7A-7C show that SH-APP (AβPP-transfected human neuroblastoma cells) transfected cells treated with HIV showed significant upregulation of Aβ-production (30.7%) using Aβ 1-40 specific primary antibody (FIG. 7B) compared to untreated control culture (8.8%) (FIG. 7A). However, WA significantly decreased HIV-induced Aβ levels (FIG. 7C), suggesting a therapeutic potential against amyloidogenesis.

AβPP-transfected SH-APP cells are susceptible to HIV infection. FIG. 8A shows that at transcriptional level WA (2 µm) reduces HIV induced LTR copies from 30,000 to 400 in SH-APP cells. Additionally, p24 ELISA shows an increase in p24 level in HIV exposed SH-APP cells (FIG. 8B).

Human neuroblastoma cells transfected with APP gene (SH-APP) were cultured with different concentrations of WA (0.5 to 2.5 µM) and the culture supernatants were tested for Aβ 1-40 by ELISA. FIG. 9A shows that WA demonstrates a dose dependent decrease of Aβ secretion by SH-APP cells at concentrations that do not show any cytotoxic effects (FIG. 9B). Based on these results, WA at 2 µM can be used for the development of nanoformulation experiments for SH-APP cells.

REFERENCES

1. Green, D. A., et al., *Brain deposition of beta-amyloid is a common pathologic feature in HIV positive patients.* Aids, 2005, 19(4): p. 407-411.
2. Dickson, D. W., et al., *Central nervous system pathology in pediatric AIDS.* Ann N Y Acad Sci, 1993, 693: p. 93-106.
3. Adle, B., et al., *Neuronal apoptosis does not correlate with dementia in HIV infection but is related to microglial activation and axonal damage.* Neuropathology and Applied Neurobiology, 1999, 25(2): p. 123-133.
4. Fiala, M., et al., *Cocaine enhances monocyte migration across the blood-brain barrier. Cocaine's connection to AIDS dementia and vasculitis?* Adv Exp Med Biol, 1998, 437: p. 199-205.
5. Gannon, P., M. Z. Khan, and D. L. Kolson, *Current understanding of HIV-associated neurocognitive disorders pathogenesis.* Curr Opin Neurol, 2011, 24(3): p. 275-83.
6. Buch, S., et al., *Cocaine and HIV-I interplay in CNS: cellular and molecular mechanisms.* Curr HIV Res, 2012, 10(5): p. 425-8.

7. Nair, M., et al., *Externally controlled on-demand release of anti-HIV drug using magneto-electric nanoparticles as carriers*. Nature communications, 2013. 4: p. 1707.
8. Antinori, A., et al., *Updated research nosology for HIV-associated neurocognitive disorders*. Neurology, 2007, 69(18): p. 1789-99.
9. McArthur, J. C. and B. J. Brew, *HIV-associated neurocognitive disorders: is there a hidden epidemic?* Aids, 2010, 24(9): p. 1367-70.
10. Giunta, B., et al., *Antiretroviral medications disrupt microglial phagocytosis of β-amyloid and increase its production by neurons: Implications for HIV-associated neurocognitive disorders*. Molecular Brain, 2011, 4: p. 23-23.
11. Husebekk, A., H. Permin, and G. Husby, *Serum amyloid protein A (SAA): an indicator of inflammation in AIDS and AIDS-related complex (ARC)*. Scand J Infect Dis, 1986, 18(5): p. 389-94.
12. Giometto, B., et al., *Accumulation of beta-amyloid precursor protein in HIV encephalitis: relationship with neuropsychological abnormalities*. Ann Neurol, 1997, 42(1): p. 34-40.
13. Rempel, H. C. and L. Pulliam, *HIV-1 Tat inhibits neprilysin and elevates amyloid beta*. Aids, 2005, 19(2): p. 127-35.
14. Achim, C. L., et al., *Increased accumulation of intraneuronal amyloid beta in HIV-infected patients*. J Neuroimmune Pharmacol, 2009, 4(2): p. 190-9.
15. Esiri, M. M., S. C. Biddolph, and C. S. Morris, *Prevalence of Alzheimer plaques in AIDS*. J Neurol Neurosurg Psychiatry, 1998, 65(1): p. 29-33.
16. Liu, S. J., et al., *Alzheimer-like phosphorylation of tau and neurofilament induced by cocaine in vivo*. Acta Pharmacol Sin, 2003, 24(6): p. 512-8.
17. Mohan, R., et al., *Withaferin A is a potent inhibitor of angiogenesis*. Angiogenesis, 2004, 7(2): p. 115-22.
18. Mirjalili, M. H., et al., *Steroidal lactones from Withania somnifera, an ancient plant for novel medicine*. Molecules, 2009, 14(7): p. 2373-93.
19. Winters, M., *Ancient medicine, modern use: Withania somnifera and its potential role in integrative oncology*. Altern Med Rev, 2006, 11(4): p. 269-77.
20. Mishra, L. C., B. B. Singh, and S. Dagenais, *Scientific basis for the therapeutic use of Withania somnifera (ashwagandha): a review*. Altern Med Rev, 2000, 5(4): p. 334-46.
21. Yelamanchili, S. V., et al., *MicroRNA-21 dysregulates the expression of MEF2C in neurons in monkey and human SIV/HIV neurological disease*. Cell Death Dis, 2010, 1: p. e77.
22. Tatro, E. T., et al., *Evidence for Alteration of Gene Regulatory Networks through MicroRNAs of the HIV-Infected Brain: Novel Analysis of Retrospective Cases*. PLOS ONE, 2010, 5(4): p. e10337.
23. Nelson, P. T. and W.-X. Wang, *MiR-107 is reduced in Alzheimer's disease brain neocortex: validation study*. Journal of Alzheimer's disease: JAD, 2010, 21(1): p. 75-79.
24. Wang, W.-X., et al., *The Expression of MicroRNA miR-107 Decreases Early in Alzheimer's Disease and May Accelerate Disease Progression through Regulation of β-Site Amyloid Precursor Protein-Cleaving Enzyme 1*. The Journal of neuroscience: the official journal of the Society for Neuroscience, 2008, 28(5): p. 1213-1223.
25. Liu, Y., et al., *Cocaine up-regulates Fra-2 and sigma-1 receptor gene and protein expression in brain regions involved in addiction and reward*. J Pharmacol Exp Ther, 2005, 314(2): p. 770-9.
26. Liu, Y. and R. R. Matsumoto, *Alterations in fos-related antigen 2 and sigmal receptor gene and protein expression are associated with the development of cocaine-induced behavioral sensitization: time course and regional distribution studies*. J Pharmacol Exp Ther, 2008, 327(1): p, 187-95.
27. Matsumoto, R. R., et al., *Conformationally restricted analogs of BD1008 and an antisense oligodeoxynucleotide targeting sigmal receptors produce anti-cocaine effects in mice*. Eur J Pharmacol, 2001, 419(2-3): p. 163-74.
28. Nair, M., et al., *Getting into the brain: Potential of nanotechnology in the management of NeuroAIDS*. Adv Drug Deliv Rev, 2016, 103: p. 202-17.
29. Sagar, V., et al., *Towards nanomedicines for neuroAIDS*. Rev Med Virol, 2014, 24(2): p. 103-24.
30. Saiyed, Z. M., N. H. Gandhi, and M. P. Nair, *Magnetic nanoformulation of azidothymidine 5-triphosphate for targeted delivery across the blood-brain barrier*. International Journal of Nanomedicine, 2010, 5: p. 157.
31. Kaushik, A., et al., *Magnetically guided central nervous system delivery and toxicity evaluation of magneto-electric nanocarriers*. Sci Rep, 2016, 6: p. 25309.
32. Guduru, R., et al., *Magneto-electric Nanoparticles to Enable Field-controlled High-Specificity Drug Delivery to Eradicate Ovarian Cancer Cells*. Nature Scientific Reports, 2013, 3.
33. Jayant, R., et al., *Sustained-release nanoART formulation for the treatment of neuroAIDS*. International Journal of Nanomedicine, 2015, 10: p. 1077-1093.
34. Tremblay, M.-E., M. Riad, and A. Majewska, *Preparation of mouse brain tissue for immunoelectron microscopy*. Journal of visualized experiments: JoVE, 2010(41).
35. Bhardwaj, V., S. Srinivasan, and A. J. McGoron, *Efficient intracellular delivery and improved biocompatibility of colloidal silver nanoparticles towards intracellular SERS immuno-sensing*. Analyst, 2015.
36. Samikkannu, T., V. S. Atluri, and M. P. Nair, *HIV and Cocaine Impact Glial Metabolism: Energy Sensor AMP-activated protein kinase Role in Mitochondrial Biogenesis and Epigenetic Remodeling*. Sci Rep, 2016, 6: p. 31784.
37. Gandhi, N., et al., *Interactive role of human immunodeficiency virus type 1 (HIV-1) clade-specific Tat protein and cocaine in blood-brain barrier dysfunction: implications for HIV-1-associated neurocognitive disorder*. J Neurovirol, 2010, 16(4): p. 294-305.
38. Reynolds, J. L., et al., *Proteomic analysis of the effects of cocaine on the enhancement of HIV-1 replication in normal human astrocytes (NHA)*. Brain Res, 2006, 1123(1): p. 226-36.
39. Ben Halima, S., et al., *Specific Inhibition of β-Secretase Processing of the Alzheimer Disease Amyloid Precursor Protein*. Cell Reports, 2016, 14(9): p. 2127-2141.
40. Ding, H., et al., *Enhanced blood-brain barrier transmigration using a novel transferrin embedded fluorescent magneto-liposome nanoformulation*. Nanotechnology, 2014, 25(5): p. 055101.
41. Persidsky, Y., et al., *A model for monocyte migration through the blood-brain barrier during HIV-1 encephalitis*. The Journal of Immunology, 1997, 158(7): p. 3499-510.

42. Hayashi, K., et al., *HIV-TAT protein upregulates expression of multidrug resistance protein 1 in the blood-brain barrier.* J Cereb Blood Flow Metab, 2006, 26(8): p. 1052-65.
43. Radde, R., et al., *Abeta42-driven cerebral amyloidosis in transgenic mice reveals early and robust pathology.* EMBO Rep, 2006, 7(9): p. 940-6.
44. Horger, B. A., et al., *Enhancement of locomotor activity and conditioned reward to cocaine by brain-derived neurotrophic factor.* J Neurosci, 1999, 19(10): p. 4110-22.
45. Pu, H., et al., *HIV-1 Tat protein-induced alterations of ZO-1 expression are mediated by redox-regulated ERK 1/2 activation.* J Cereb Blood Flow Metab, 2005, 25(10): p. 1325-35.
46. Maragos, W. F., et al., *Neuronal injury in hippocampus with human immunodeficiency virus transactivating protein, Tat.* Neuroscience, 2003, 117(1): p. 43-53.
47. Pu, H., et al., *HIV-1 tat protein upregulates inflammatory mediators and induces monocyte invasion into the brain.* Molecular and Cellular Neuroscience, 2003, 24(1): p. 224-237.
48. Carrera, I., et al., *Vaccine Development to Treat Alzheimer's Disease Neuropathology in APP/PS1 Transgenic Mice.* Int J Alzheimers Dis, 2012, 2012: p. 376138.
49. Antunes, M. and G. Biala, *The novel object recognition memory: neurobiology, test procedure, and its modifications.* Cognitive Processing, 2012, 13(2): p. 93-110.
50. Potash, M. J., et al., *A mouse model for study of systemic HIV-1 infection, antiviral immune responses, and neuroinvasiveness.* Proc Natl Acad Sci USA, 2005, 102(10): p. 3760-5.
51. Jones, L. D., J. W. Jackson, and S. B. Maggirwar, *Modeling HIV-1 Induced Neuroinflammation in Mice: Role of Platelets in Mediating Blood-Brain Barrier Dysfunction.* PLOS ONE, 2016, 11(3): p. e0151702.
52. He, H., et al., *Enhanced human immunodeficiency virus Type 1 expression and neuropathogenesis in knockout mice lacking Type I interferon responses.* J Neuropathol Exp Neurol, 2014, 73(1): p. 59-71.
53. Kelschenbach, J. L., et al., *Mice chronically infected with chimeric HIV resist peripheral and brain superinfection: a model of protective immunity to HIV.* J Neuroimmune Pharmacol, 2012, 7(2): p. 380-7.
54. Hadas, E., et al., *Transmission of chimeric HIV by mating in conventional mice: prevention by pre-exposure antiretroviral therapy and reduced susceptibility during estrus.* Dis Model Mech, 2013, 6(5): p. 1292-8.
55. Moidunny, S., et al., *Oncostatin M promotes excitotoxicity by inhibiting glutamate uptake in astrocytes: implications in HIV-associated neurotoxicity.* J Neuroinflammation, 2016, 13(1): p. 144.
56. Bertrand L, D. L., Toborek M., *Induction of ischemic stroke and ischemia-reperfusion in mice using the middle artery occlusion technique and visualization of infract area.* JoVE, In Press.
57. Bertrand L, Toborek M., *Antiretroviral treatment with efavirenz disrupts the blood-brain barrier integrity and increases stroke severity.* Scientific Reports, In Press.
58. Lackner, A. A., et al., *Early events in tissues during infection with pathogenic (SIVmac239) and nonpathogenic (SIVmac1All) molecular clones of simian immunodeficiency virus.* Am J Pathol, 1994, 145(2): p. 428-39.
59. Davis, L. E., et al., *Early viral brain invasion in iatrogenic human immunodeficiency virus infection.* Neurology, 1992, 42(9): p. 1736-9.
60. Stephens, E. B., et al., *The primary phase of infection by pathogenic simian-human immunodeficiency virus results in disruption of the blood-brain barrier.* AIDS Res Hum Retroviruses, 2003, 19(10): p. 837-46.
61. Wright, P. W., et al., *Cerebral white matter integrity during primary HIV infection.* AIDS, 2015, 29(4): p. 433-42.
62. Peluso, M. J., et al., *Cerebrospinal fluid and neuroimaging biomarker abnormalities suggest early neurological injury in a subset of individuals during primary HIV infection.* J Infect Dis, 2013, 207(11): p. 1703-12.
63. Li, S., et al., *Matrix metalloproteinase levels in early HIV infection and relation to in vivo brain status.* J Neurovirol, 2013, 19(5): p. 452-60.

We claim:

1. A formulation comprising magnetic nanoparticles (MENPs) conjugated to or mixed with a therapeutic cargo, the therapeutic cargo comprising withaferin A (WA), miR-107 or an expression vector encoding miR-107, and BD1063, at least a portion of the MENPs surface being coated with one or more of glycerol monooleate, poly L-lysine and polyethylene glycol, the MENPs being encapsulated within liposomes; WA being in a hydrophobic part of the liposome, miR-107 or an expression vector encoding miR-107 bound to the MENPs based on electrostatic interaction, and BD1063 being in a hydrophilic part of the liposome.

2. The formulation of claim 1, wherein the MENPs comprise $CoFe_2O_4$—$BaTiO_3$.

3. The formulation of claim 1, wherein the MENPs are formed from a material selected from iron, cobalt, zinc, cadmium, nickel, gadolinium, chromium, copper, manganese, terbium, europium, gold, silver, platinum, oxides thereof, and mixtures thereof.

4. The formulation of claim 1, the miR-107 being a primary miR-107, pre-miR-107, or mature miR-107.

5. The formulation of claim 1, the MENPs comprising a multiferroic material that couples magnetic and electric fields at room temperature.

6. The formulation of claim 1, the MENPs comprising iron oxide, superparamagnetic iron oxide, $Fe_3O_4$, or $Fe_2O_4$.

7. The formulation of claim 1, the MENPs being smaller than 50 nm.

8. The formulation of claim 1, the liposomes being surface modified with an affinity ligand that targets the liposomes to the brain.

9. A method of treating an HIV infection in a subject having cocaine addiction, the method comprising administering to the subject the formulation of claim 1, the method further comprising applying to the subject magnetic forces to guide the MENPs across the blood brain barrier and into brain parenchyma and releasing the therapeutic cargo into the brain parenchyma by applying to the subject an alternating current.

10. A formulation comprising MENPs conjugated to or mixed with a therapeutic cargo, the therapeutic cargo comprising withaferin A (WA), miR-107 or an expression vector encoding miR-107, and BD1063; the MENPs being encapsulated within liposomes; WA being in a hydrophobic part of the liposome, miR-107 or an expression vector encoding miR-107 bound to the MENPs based on electrostatic interaction, and BD1063 being in a hydrophilic part of the liposome.

11. The formulation of claim 10, the miR-107 being a primary miR-107, pre-miR-107, or mature miR-107.

12. The formulation of claim 10, the MENPs comprising a multiferroic material that couples magnetic and electric fields at room temperature.

13. The formulation of claim 10, the MENPs comprising iron oxide, superparamagnetic iron oxide, $Fe_3O_4$, or $Fe_2O_4$.

14. The formulation of claim 10, the MENPs comprising $CoFe_2O_4$—$BaTiO_3$.

15. The formulation of claim 10, wherein the MENPs are formed from a material selected from iron, cobalt, zinc, cadmium, nickel, gadolinium, chromium, copper, manganese, terbium, europium, gold, silver, platinum, oxides thereof, and mixtures thereof.

16. The formulation of claim 10, the liposomes being surface modified with an affinity ligand that targets the liposomes to the brain.

17. The formulation of claim 16, the affinity ligand being a polyclonal or monoclonal antibody, peptide, or peptidomimetic.

18. A method of treating an HIV infection in a subject having cocaine addiction, the method comprising administering to the subject the formulation of claim 10, the method further comprising applying to the subject magnetic forces to guide the MENPs across the blood brain barrier and into brain parenchyma and releasing the therapeutic cargo into the brain parenchyma by applying to the subject an alternating current.

19. A method of treating an HIV infection in a subject having cocaine addiction, the method comprising administering to the subject the formulation of claim 10.

20. The method of claim 19, the method further comprising applying to the subject magnetic forces to guide the MENPs across the blood brain barrier and into brain parenchyma and releasing the therapeutic cargo into the brain parenchyma by applying to the subject an alternating current.

* * * * *

UNITED STATES PATENT AND TRADEMARK OFFICE
CERTIFICATE OF CORRECTION

| | | |
|---|---|---|
| PATENT NO. | : 10,213,507 B2 | Page 1 of 1 |
| APPLICATION NO. | : 15/456039 | |
| DATED | : February 26, 2019 | |
| INVENTOR(S) | : Madhavan Nair, Sneham Tiwari and Adriana Yndart Arias | |

It is certified that error appears in the above-identified patent and that said Letters Patent is hereby corrected as shown below:

In the Specification

<u>Column 1, Lines 7-10</u>:
"This invention was made with government support under RO1-DA040537, RO1-DA037838, and RO1-DA042706-A awarded by National Institute of Health. The government has certain rights in the invention."

Should read:
--This invention was made with government support under DA040537, DA037838, and DA042706, awarded by the National Institutes of Health. The government has certain rights in the invention.--

Signed and Sealed this
Twenty-fifth Day of June, 2019

Andrei Iancu
*Director of the United States Patent and Trademark Office*